(12) United States Patent
Sippel et al.

(10) Patent No.: US 7,029,905 B1
(45) Date of Patent: Apr. 18, 2006

(54) METHOD FOR THE CELLULAR HIGH-THROUGHPUT-DETECTION OF RECEPTOR LIGAND INTERACTIONS

(76) Inventors: Albright E. Sippel, Tivolistrasse 5, Freiburg (DE) D-79104; André Zimmermann, Talstrasse 4, Freiburg (DE) D-79102

( * ) Notice: Subject to any disclaimer, the term of this patent is extended or adjusted under 35 U.S.C. 154(b) by 0 days.

(21) Appl. No.: 09/869,709

(22) PCT Filed: Dec. 20, 1999

(86) PCT No.: PCT/EP99/10400

§ 371 (c)(1),
(2), (4) Date: Oct. 18, 2001

(87) PCT Pub. No.: WO00/40969

PCT Pub. Date: Jul. 13, 2000

(30) Foreign Application Priority Data

Dec. 30, 1998 (DE) ................................ 198 60 833

(51) Int. Cl.
C12N 1/14 (2006.01)
C12N 1/15 (2006.01)
C12N 1/16 (2006.01)
C12Q 1/00 (2006.01)
C12Q 1/02 (2006.01)

(52) U.S. Cl. ............................... 435/254.2; 243/254.1; 243/255.1; 243/4; 243/7.1; 243/7.2; 536/23.2; 536/23.4; 536/23.5

(58) Field of Classification Search ............... 536/23.2, 536/23.5, 23.7; 435/4, 6, 7.1, 7.2, 7.31, 7.9, 435/29, 471, 243, 252.3, 254.1, 254.11, 254.2, 435/254.21, 255.1, 255.2, 325, 361, 320.1, 435/69.1, 287.1, 287.2, 288.7, 356, 7.21; 530/350, 349, 351, 23.4, 25.32, 399; 424/278.1, 424/9.2, 9.1; 422/55
See application file for complete search history.

(56) References Cited

U.S. PATENT DOCUMENTS

| | | | | |
|---|---|---|---|---|
| 5,521,295 A | * | 5/1996 | Pacifici et al. ............. | 536/23.4 |
| 5,532,157 A | * | 7/1996 | Fink ........................... | 435/356 |
| 5,569,588 A | * | 10/1996 | Ashby et al. .................. | 435/6 |
| 6,159,705 A | * | 12/2000 | Trueheart et al. ............. | 435/29 |
| 6,251,605 B1 | * | 6/2001 | Ostanin et al. ................ | 435/6 |
| 6,391,574 B1 | * | 5/2002 | Rine et al. ..................... | 435/23 |
| 2003/0009022 A1 | * | 1/2003 | Klein et al. ................. | 536/23.5 |

FOREIGN PATENT DOCUMENTS

| | | | |
|---|---|---|---|
| EP | | 0863214 A | 9/1998 |
| WO | | WO 9307294 A | 4/1993 |
| WO | | WO 94/29458 | * 12/1994 |
| WO | | WO 9523231 A | 8/1995 |
| WO | | WO 9746688 A | 12/1997 |
| WO | | WO 9748820 A | 12/1997 |
| WO | | WO 98/26054 | * 6/1998 |
| WO | | WO 9826054 A | 6/1998 |
| WO | | WO 9902675 A | 1/1999 |

OTHER PUBLICATIONS

Isakoff et al., EMBO Journal, vol. 17, No. 18, pp. 5374-5387 (Sep. 1998).*
Aronheim et al., Molecular and Cell Biology, vol. 17, No. 6, pp. 3094-3102 (Jun. 1997).*
Aronheim, Ami, Nucleic Acids Research, vol. 25, No. 16, pp. 3373-3374 (Aug. 1997).*
Mitsuzawa et al., Genetics, vol. 123, pp. 739-748 (Dec. 1989).*
DeClue et al, Molecular and Cellular Biology, vol. 11, No. 6, pp. 3132-3138 (Jun. 1991).*
Bai et al., Oncogene vol. 17, No. 8, pp. 941-948 (Aug. 1998).*
Wadsworth et al., The Journal of Biological Chemistry, vol. 272, No. 46 (Nov. 1997).*
Jiang et al., Natur , vol. 395, No. 6704, pp. 808-813 (Oct. 1998).*
Bence et al., Nature, vol. 389, No. 6648, pp. 296-299 (Sep. 1997).*
Yang et al., Journal of Biological Chemistry, vol. 270, No. 35, pp. 20832-20840 (Sep. 1995).*
Kawakami et al., Journal of Immunology, vol. 161, No. 4, pp. 1795-1802 (Aug. 1998).*
Ngo et al., from The Protein Folding Problem and Tertiary Structure Prediction, Merz et al. (eds), Birkhauser, Boston 1994, pp. 433-506.*
Bowie, et al., Science, vol. 247, pp. 1306-1310 (1990).*
Wells, Biochemistry, vol. 29, No. 37, pp. 8509-8517 (Sep. 1990).*

(Continued)

*Primary Examiner*—James C. Housel
*Assistant Examiner*—Zachariah Lucas
(74) *Attorney, Agent, or Firm*—Millen, White, Zelano & Branigan, P.C.

(57) ABSTRACT

The invention relates to cells which comprise a membrane receptor which comprises a ligand-binding section, a membrane-localization signal and a mediator section, and which is characterized in that only when there is binding or, alternatively, only when there is a lack of binding of a ligand to the ligand-binding section of the membrane receptor is a structural change brought about with effects on the mediator section to result in binding of an effector protein or polypeptide, which is capable of activating a Ras or Ras-like signal pathway in the cell, to the component of the membrane, where appropriate via other proteins or polypeptides (adaptors). It further relates to assay methods employing these cells, which are used, inter alia, to detect specific interactions between said membrane receptor and a ligand, and kits for use in these assays.

26 Claims, 4 Drawing Sheets

OTHER PUBLICATIONS

Rawlings et al., Science, vol. 271, No. 5250, pp. 822-825 (Feb. 1996).*
Lodish et al., Mol cular Cell Biology, 3rd Ed, Scientific American Books, N.Y. (1995), pp. 859, and 862-863.*
Wu et al., Journal of Biological Chemistry, vol. 273, No. 13, pp. 7197-7200 (Mar. 1998).*
Freedman et al., Journal of Biological Chemistry, vol. 277, No. 50, pp. 48261-48269 (Dec. 2002).*
Delorme, E., Applied and Environmental Microbiology, vol. 55(9): pp. 2242-2246 (1989).*
Li et al., Journal of Biological Chemistry, vol. 272 No. 16, pp. 10337-10340 (1997).*
Baldari et al., Journal of Biological Chemistry, vol. 267, No. 7, pp. 4289-4291 (1992).*
Schlessinger, Trends in Biochemical Science, vol. 18, pp. 273-275 (1993).*
Suen et al., Molecular and Cellular Biology, Colume 13 No. 9, pp. 5500-5512 (Sep. 1993).*
Rozakis-Adcock et al., Naure, vol. 363 No. 6424, pp. 83-85 (May 1993).*
Hart et al., Oncogene, Volum 14 No. 8, pp. 945-953 (Feb. 1997).*
Buss et al., Science, vol. 243 No. 4898, pp. 1600-1603 (Mar. 1989).*
Lemmon et al., The Journal of Bological Chemistry, vol. 269 No. 50, pp. 31653-31658 (Dec. 1994).*
Willumsen et al., The EMBO Journal, vol. 3 No. 11, pp. 2581-2585 (1984).*

* cited by examiner

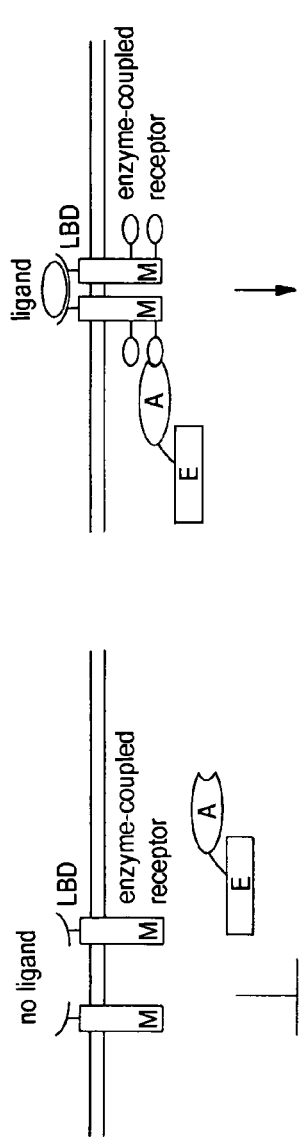
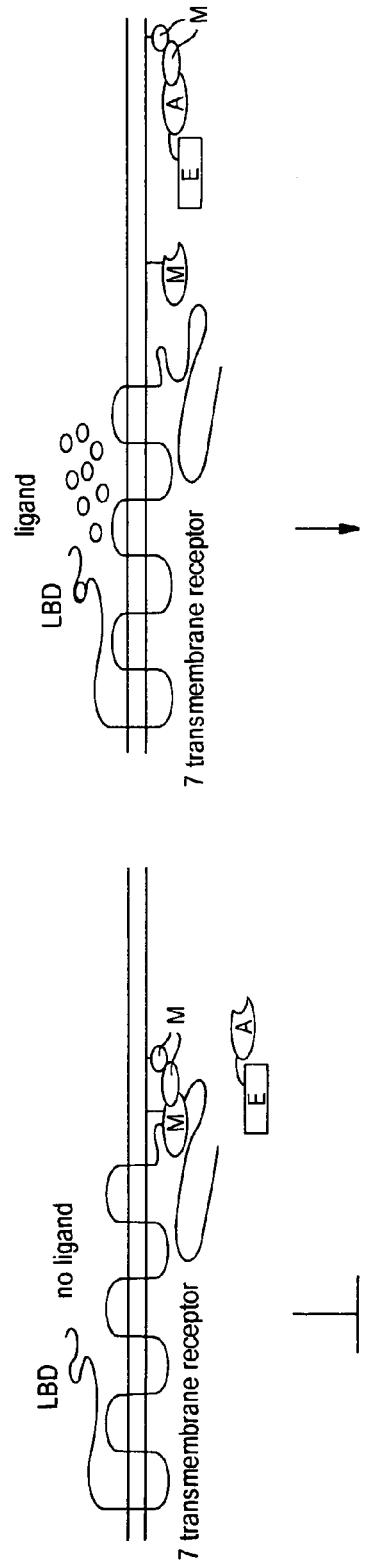
FIG. 2a
FIG. 2b

METHOD FOR THE CELLULAR HIGH-THROUGHPUT-DETECTION OF RECEPTOR LIGAND INTERACTIONS

The invention relates to the area of molecular biology. It relates in particular to assay methods which are used to detect specific interactions between an extracellular ligand and an, in particular, membrane-associated receptor, and aims inter alia at finding novel functional ligands for receptors and, where appropriate, detecting a ligand-binding function which is characteristic of, in particular, membrane-associated receptors, in polypeptides or proteins suspected of such a function. In this connection, the invention also relates to membrane receptors, in particular fusion proteins, nucleic acids which encode these membrane receptors, in particular fusion proteins, vectors which comprise these nucleic acids, cells which comprise these membrane receptors, in particular fusion proteins, and kits, all of which can be employed for the assay methods of the invention or in connection with the latter.

Cells, particularly cells in multicellular organisms, are dependant on responding appropriately to extracellular signals from their surroundings. Signal target cells make use of membrane-associated receptor proteins for specific signal reception. Binding of extracellular ligand molecules to the extracellular sections of the receptor (ligand-binding section) leads to a conformation-mediated relaying of the signal through the transmembrane region of the receptor to the cytoplasmic section of the receptor in the interior of the cell (mediator section). It is thus possible for the ligand binding-dependant molecular chain to be picked up by adaptor molecules on the cytoplasmic side of the receptor and relayed to signal transduction pathways inside the cell (FIG. 1). The effects of receptor-mediated signal transduction are rapid changes in cytoplasmic structures and processes altering gene activity and the replication or breakdown of genetic material in the cell nucleus.

Membrane receptors thus mediate their intracellular relaying of signals via the cytoplasmic mediator section of the receptor. Depending on the characteristics of this mediator section, the membrane receptors are divided into those where the relaying of the signal by the mediator takes place via an enzymatic protein kinase reaction (enzyme-coupled receptors) or via so-called G proteins (G-protein-coupled receptors).

The enzyme-coupled receptors include those where the enzymatically active mediator section is located directly in the same receptor protein molecule which also carries the ligand-binding section. A classic example of this type of receptor is the epidermal growth factor (EGF) receptor (Schlessinger and Ulrich, 1992). With other enzyme-coupled receptors, the enzymatically active protein section is located in a second protein subunit. Classic examples of this type are many cytokine receptors (Stahl and Yancopoulos, 1993). It is common to all of them that the protein kinase activity of the mediator section of the receptor is strictly dependant on the binding of the ligand to the ligand-binding domain of the receptor. Many of the enzyme-coupled receptors transmit their signal via adaptor proteins and polypeptides to members of the ras family of monomeric GTPases which are able, inter alia, to activate a serine/threonine phosphorylation cascade (Nishida and Gotoh, 1993).

With the G-protein-coupled receptors, the cytoplasmic receptor configuration depending on ligand binding is picked up by a G-protein complex which consists of three subunits and which relays the signal by dissociation into an activated membrane-bound βγ part and into an activated Gα protein subunit. During this, the Gα protein subunit exchanges its cofactor GTP which is characteristic of the inactive state for the cofactor GTP which is characteristic of the activated state and which, after GTP to GDP hydrolysis, reinactivates the Gα protein subunit. A wide variety of signal transfection pathways is coupled to this cycle via the activated βγ subunit and/or the activated α subunit of the G-protein complex as mediators. The G-protein-coupled receptors include the large family of 7-transmembrane receptors. These include, for example, the toxin receptors, the odor receptors, neurotransmitter receptors and many hundreds more (Dohlman et al., 1991, Leurs et al., 1998). Examples of adaptor proteins for the G-protein mediators are adenylate cyclases, phospholipase C and other G-protein-coupled receptor kinases, and certain ion channels.

Membrane receptor-mediated signal transductions control the crucial intracellular processes for survival of the cells, for growth and cell division, for cell differentiation and for cell death (apoptosis). Errors in the important control pathways induced by mutations frequently contribute to the development of disease, and in particular, of cancer. It is understandable why the ligand-receptor interaction is of great scientific, pharmaceutical and commercial interest because it represents the principal point of contact between extracellular surroundings and intracellular events in all living cells. It is possible with the aid of the ligand molecules to intervene from outside in a natural way in virtually all important intracellular processes and take countermeasures if there are faulty developments. The effect of many pharmaceuticals is based on their function as agonists or antagonists of naturally occurring ligands. It is understandable why there is great interest in being able to detect and study such receptor-ligand interactions at the molecular level.

A number of methods for detecting membrane receptor-ligand interactions already exists. One of the methods makes use of the fact that many receptors have, because of their evolutionary relationship, very similar structures and their functional parts of proteins, called domains, can easily be interchanged and fused together in a new arrangement. It is thus possible for a wide variety of extracellular ligand-binding domains to be linked to specific cytosolic reporter domains in order to create certain standardizations in the detection system in cells (see, for example, U.S. Pat. No. 4,859,609). The disadvantage of this method derives from the need to construct functional recombinant receptor fusion proteins which respond selectively to the receptor-ligand interaction to be tested in cells.

Another approach to the study of membrane receptor-ligand interactions starts from unmodified wild-type receptors but makes use of antibodies directed against the specific configurational states of the cytosolic receptor domains in order to measure the ligand interactions.

A further approach detects the receptor-ligand interaction ex vivo, i.e. outside the living cell, by attaching either extracellular receptor domains or the ligand molecule to a matrix over which a solution containing the ligand or the receptor, respectively, then flows. In this case, the effort for obtaining and attaching each individual receptor or ligand to the appropriate matrix surface is enormous. Another problem in this connection is also the extrapolation of the results obtained to the conditions in the membrane of the living cells, because the cellular conditions may differ considerably from the ex vivo conditions. However, the most serious problem in this connection is the lack of possibility of access to the genetic information of the novel receptor variants detected in screens or high-throughput assays.

BRIEF DESCRIPTION OF THE DRAWINGS

FIG. 2 (A and B). Diagrammatic representation of a ligand-membrane receptor interaction of an enzyme-coupled and of a G-protein-coupled receptor.

DESCRIPTION OF THE INVENTION

Figure 1:
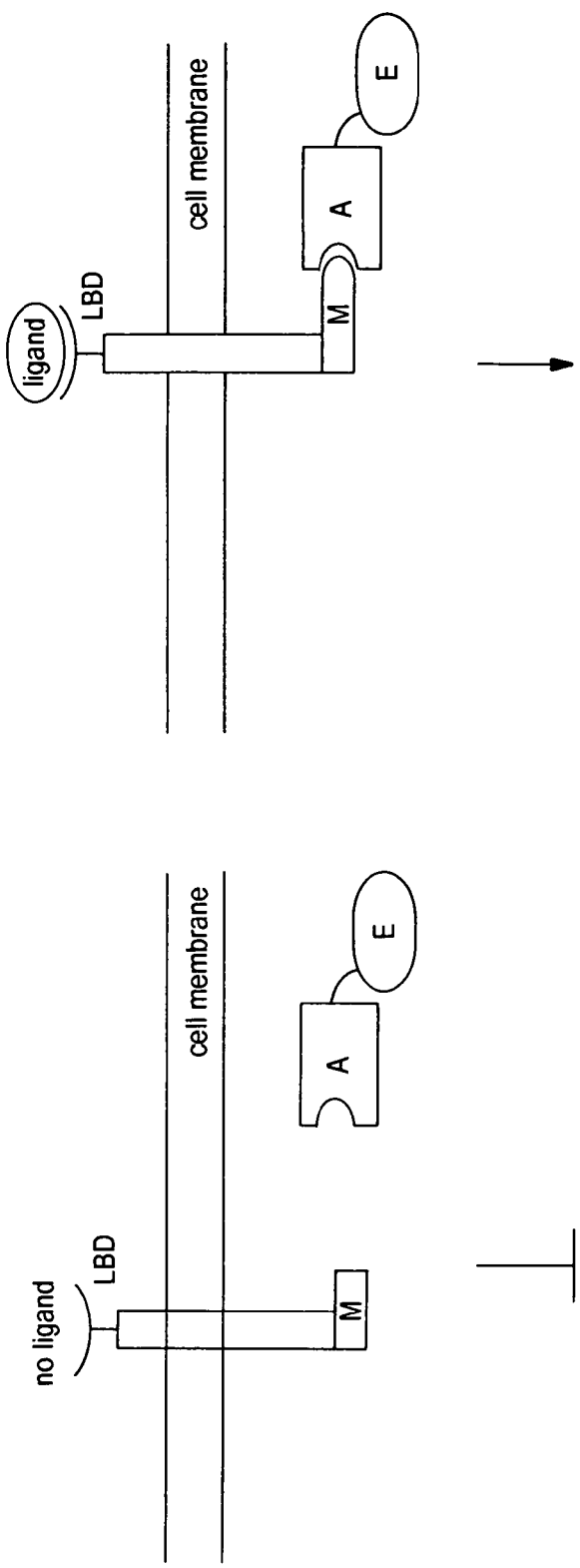
FIG. 1. Diagrammatic representation of the detection of a ligand-membrane receptor interaction.

The object on which the invention is based is to provide alternative assays suitable for detecting in vivo specific interactions between a ligand and an in particular membrane-associated receptor, which has, inter alia, the advantages of being able to detect ligand-receptor interactions more quickly than possible in the prior art, and being capable of being carried out using cells which are simple to manipulate, such as prokaryotic cells or yeast cells, or else using ghost forms, lacking cell walls, of, in particular, yeasts. In addition, because of the design of the assay, there is always a direct possibility of access to the genetic information underlying a receptor variant.

Further objects of the invention comprise the provision of cells, kits, membrane receptors, in particular fusion proteins, nucleic acids and vectors, all of which can be employed for the assay methods of the invention or in conjunction with the latter.

The objects on which the invention is based are met by the assay methods, kits, cells, fusion proteins, nucleic acids and vectors defined in the claims.

The present invention is based on the following realizations:

1. With every membrane receptor, the binding of the ligand initiates a change of configurational state in the extracellular domain and/or a covalent modification in the cytosolic part.

2. For every membrane receptor there are cytosolic adaptor proteins which are near the membrane or membrane-associated and are able to recognize the ligand-specific configurational changes or activated as a consequence thereof.

3. The membrane localization of certain components of the signal pathways is necessary for activation of various ras and ras-like signal transduction pathways (Schlessinger, TIBS, 18: 273–275, 1993).

4.a) If a protein from the Ras family or a guanine nucleotide exchange factor (GEF) is provided as effector protein or polypeptide in such a way that it is able to bind as a result of ligand binding to the extracellular domain of a membrane receptor to one component of the membrane, for example to the intracellular section (=mediator section) of the membrane receptor or to adaptor proteins located near the membrane or associated with the membrane, for which purpose it is provided where appropriate as fusion protein whose additional protein portion, which can also be referred to as adaptor section, makes binding possible to such a component of the membrane, in the event of such a binding the Ras protein or the GEF undergoes membrane localization which is necessary for activation of a ras or ras-like signal transduction pathway.

4.b) An alternative possibility is for a protein from the Ras family or a guanine nucleotide exchange factor (GEF) to be provided as effector protein or polypeptide in such a way that it is able to bind only as a result of a lack of ligand binding to the extracellular domain of a membrane receptor to a component of the membrane, for example to the intracellular section (=mediator section) of the membrane receptor or to adaptor proteins located near the membrane or associated with the membrane, for which purpose it is provided where appropriate as fusion protein whose additional protein portion, which can also be referred to as adaptor section, makes binding possible to such a component of the membrane. Because of such a binding, which in this variant is made possible only when there is a lack of ligand binding to the extracellular domain of the membrane receptor, the Ras protein or the GEF then undergoes membrane localization which is necessary for activation of a ras or ras-like signal transduction pathway.

5. A result of such a membrane receptor-ligand interaction can be detected in eukaryotic and, where appropriate, also prokaryotic cells. Cells in which a ras or ras-like signal transduction pathway can be inactivated at least under certain conditions at the level of the Ras protein specific therefor or of a guanine nucleotide exchange factor specific for the Ras protein are known in the prior art. If the effector protein or polypeptide explained under 4. is able in such a cell to activate precisely this inactivated signal pathway, the result is a cell in which the ras or ras-like signal transduction pathway which is intrinsic to the cell and which is inactive at least under certain conditions can be activated by this Ras protein—although in the case of variant 4.a) only in the presence of a ligand for the extracellular ligand-binding section of the membrane receptor, and in the case of variant 4.b) only in the absence of a ligand for the extracellular ligand-binding section of the membrane receptor.

This results in a cell in which the or a particular ras signal transduction pathway can be activated only as a function of a ligand binding to the ligand-binding section of a membrane-associated receptor (variant 4.a)) or only when there is a lack of ligand binding to the ligand-binding section of a membrane-associated receptor (variant 4.b)). This cell makes it possible to establish an in vivo assay method which, on the basis of detecting an activation, which has taken place where appropriate, of the specific ras signal transduction pathway, where appropriate indirectly via specific effects detectable on or in the cell, such as cell growth, makes it possible to detect interactions between such a receptor and a ligand specific therefor.

This invention therefore relates firstly to a cell which comprises a membrane receptor which comprises a ligand-binding section, a membrane-localization signal and a mediator section, and which is characterized in that only when a ligand binds to the ligand-binding section or, alternatively, only when binding of a ligand to the ligand-binding section is lacking is a structural change, in particular a conformational change and/or an enzymatic modification, e.g. by phosphorylation or dephosphorylation, brought about with effects on the mediator section to result in binding of an effector-protein or polypeptide, which is capable of activating a Ras or Ras-like signal pathway in the cell, to a component of the cell membrane, and in particular to the mediator section of the receptor protein, where appropriate via other proteins or polypeptides.

The membrane receptor may be a naturally occurring receptor such as, for example, a transmembrane receptor, an enzyme-coupled receptor, a G-protein-coupled receptor, a 7-transmembrane receptor or an odor receptor (or olfactorial receptor). The membrane receptor may naturally occur in the cell or may originate from a cell system of a different type or else a virus and have been introduced into the cell by transformation or transfection.

An alternative possibility is for the membrane receptor also to be a non-naturally occurring, synthetic receptor. One of this type preferably comprises sections or domains which in turn each occur in nature, such as, for example, the amino acid sequence of the ligand-binding section of a transmembrane receptor, of an enzyme-coupled receptor, of a G-protein-coupled receptor, of a 7-transmembrane receptor or of an odor receptor (or olfactorial receptor), but also that of a naturally occurring nuclear receptor, such as a steroid receptor, orphan receptor, vitamin receptor, for example vitamin D receptor, thyroxin receptor or retinoic acid receptor, or that of a naturally occurring viral receptor, in particular membrane receptor, or sequences derived therefrom by amino acid attachment, exchange, modification, insertion or deletion, but may also comprise, for example, sections generated by molecular modeling. Such a membrane receptor may comprise, for example, a ligand-binding section and a membrane-localization signal, both of which originate from a particular protein from a particular organism, and a mediator section which derives from a different protein and, where appropriate, also organism. In particular, the ligand-binding section and the mediator section derive from different proteins and, where appropriate, also organisms; the membrane-localization signal may also correspondingly derive from a different protein and/or organism or else be generated synthetically. In addition, the ligand-binding section may comprise a non-naturally occurring, synthetic ligand-binding section, for example generated by molecular modeling, with in particular initially only suspected ligand-binding function.

In preferred embodiments of this invention, the membrane-localization signal of the membrane receptor comprises the amino acid sequence of a transmembrane domain as found, in particular, in transmembrane receptors, of a farnesylation signal, myristylation signal or prenylation signal or is derived therefrom for example by amino acid exchange, modification, insertion or deletion.

In the region of the membrane-localization domain or as an additional sequence section which is, in particular, located at the N terminus it is also possible to provide a signal sequence which, although it does not serve to anchor the membrane receptor in the membrane as such, has the effect that the membrane receptor is transported after expression thereof with high efficiency onto the cell membrane. The higher concentration, resulting therefrom, of membrane receptor in the immediate vicinity of the membrane results in a higher rate of incorporation of the membrane receptor into the cell membrane because of the membrane-localization domain. Such signal sequences are preferably used specifically suited to the cell type in which the membrane receptor is to be expressed because, for example, signal sequences effective in yeast are effective only with lower efficiency in mammalian cells, and vice versa. Examples of such signal sequences are signal sequences of GPCRs intrinsic to yeast or of invertase intrinsic to yeast (SUC2) for preferred use in membrane receptors which are to be expressed in yeast cells.

Accordingly, depending on the desired cell type it may also be sensible to replace a signal sequence intrinsic to the receptor by a signal sequence which is more effective in the desired cell type, for example when working in particular in yeast cells by replacing a signal sequence intrinsic to the receptor at the N terminus of a membrane receptor protein by the signal sequence of one of the G-protein-coupled receptors (GPCRs) intrinsic to yeast or a similar signal sequence which ensures that the receptor is anchored in active form in the cell membrane. In the case of receptor tyrosine kinases (RTKs) or receptor phosphatases it is possible, in particular for work in yeasts, to mention by way of example replacement of the signal sequence intrinsic to the receptor, where present, by the signal sequence with the invertase intrinsic to yeast (SUC2) or another signal sequence which optimizes the anchoring of the receptor in active form in the cell membrane.

As already mentioned, the effector protein or polypeptide which is able to activate a Ras or Ras-like signal pathway is a guanine nucleotide exchange factor (GEF), e.g. the CDC25 protein from *Saccharomyces cerevisiae* or an SOS protein from a mammal or an SOS-like protein from any organism, or an active protein from the Ras family, is derived from such factors or proteins, or has such a function in a section thereof.

In a particular embodiment which is explained in more detail hereinafter, the effector protein or polypeptide which is able to activate a Ras or Ras-like signal pathway is in the form of a fusion protein of an effector section with an adaptor protein or polypeptide which makes binding to a component of the membrane possible in the case of ligand binding to the ligand-binding section of the membrane receptor or, alternatively, only in the case of a lack of ligand binding to the ligand-binding section of the membrane receptor, where appropriate via other proteins or polypeptides.

In another specific embodiment, the fusion protein requires enzymatic modification before it can be bound to the component of the membrane, where appropriate via other proteins or polypeptides. In this case, an enzymatic activity necessary for the enzymatic modification is activated in the cell system of the invention only because of ligand binding to the ligand-binding section or, alternatively, only because of lack of ligand binding to the ligand-binding section.

In all cases, as a result of the ligand binding to the ligand-binding section of the membrane receptor or, alternatively, as a result of the lack of ligand binding to the ligand-binding section of the membrane receptor there is in the cells a translocation of the effector protein or polypeptide onto the cell membrane, which makes activation of the Ras or Ras-like signal pathway possible. The translocation is brought about because of the binding of the effector protein or polypeptide to a component of the membrane and, in a preferred embodiment of those possible, to the mediator section of the membrane receptor, where appropriate via other proteins or polypeptides. The binding of the effector protein or polypeptide to the component of the membrane is possible only-when a ligand binds to the ligand-binding section of this membrane receptor or, alternatively, only when there is a lack of binding of a ligand to the ligand-binding section of this membrane receptor, because this brings about a structural change, in particular conformational change, with effects on the mediator section, to result in the effector protein or polypeptide binding, where appropriate via other proteins or polypeptides, to the component of the membrane, and in a preferred embodiment to precisely this mediator section.

This binding of the effector protein or polypeptide to a component of the membrane, where appropriate via other proteins or polypeptides, can take place in various ways depending on the particular membrane receptor and, in particular, on the particular mediator section of the membrane receptor:

1) In a first variant, the mediator section corresponds to the cytoplasmic part of a G-protein-coupled receptor. Alternatively, it comprises sections, which are essential for the properties explained hereinafter of this part of G-protein-coupled receptors, of such receptors or else sequences which are derived from said parts or sections for example by amino acid attachment, substitution, deletion, insertion and/or modification but which still have the properties to be explained of the initial sequences.

The membrane receptor comprising said mediator section can be, for example, a naturally occurring 7-transmembrane receptor. These receptors comprise, for example, the toxin receptors, the odor receptors, neurotransmitter receptors and many others (Dohlman et al., 1991, Leurs et al., 1998).

In addition, the membrane receptor may also be a synthetic receptor, e.g. with the cytoplasmic part of a particular G-protein-coupled receptor as mediator section and with the ligand-binding domain of another G-protein-coupled receptor or else of a different type of receptor. In a specific embodiment of the invention, with synthetic receptors of this type the ligand-binding section brings about, on binding of ligand, the structural change, in particular conformational change, naturally occurring in this case with G-protein-coupled receptors, with an effect on the mediator section, the cytoplasmic part of the receptor. Alternatively, other types of structural changes with effects detectable according to the invention on the mediator section of the receptor are also conceivable on binding of ligands.

As already explained, with G-protein-coupled receptors the cytoplasmic receptor configuration depending on a ligand binding is picked up by a G-protein complex which consists of three subunits and which relays the signal by dissociation into an activated membrane-bound βγ part and activated, likewise membrane-bound, Gα protein subunit. Activation of the Gα protein subunit is associated with replacement of the cofactor GDP characteristic of the inactive state by the cofactor GTP which is characteristic of the activated state and which reinactivates the Gα protein subunit after GTP to GDP hydrolysis.

The relaying of the signal from the G-protein activation, i.e. dissociation, or inactivation, i.e. reassociation, to the G-protein mediators, various signal transduction pathways which in turn act on the metabolism, is mediated by so-called adaptor proteins. Adaptor proteins for G-protein mediators are, for example, adenylate cyclases, phospholipase C and other G-protein-coupled receptor kinases, and certain ion channels. Some of these bind in particular to the activated βγ part, which is still associated with the mediator section and therefore membrane-associated, of the G-protein, while others in turn bind to the activated Gα protein subunit which has dissociated off but is likewise still membrane-bound.

An effector protein or polypeptide translocation onto the membrane can now take place
  via mediation by the membrane-associated activated βγ part of the G-protein (variant (a)),
  via mediation by the activated Gα protein subunit which has dissociated off from the βγ part of the G-protein but is still membrane-bound (variant (b)) or
  via the mediator section of the membrane receptor in its specific structure as present after binding of a ligand to the ligand-binding section of the membrane receptor or, alternatively, when there is a lack of binding of a ligand to the ligand-binding section of the membrane receptor (variant (c)).

Variants (a) and (b):
An effector protein or polypeptide translocation onto the membrane via mediation by the membrane-associated activated βγ part of the G-protein (variant (a)) or via mediation by the activated Gα protein subunit which has dissociated off from the βγ part of the G-protein but is still membrane-bound (variant (b)) can take place
  through "binding" to the membrane-bound activated βγ part (variant (a)) or to the membrane-bound activated Gα protein subunit which has dissociated off the G-protein (variant (b)) directly (alternative (i)),
  via one of said adaptor proteins which are associated with the membrane-associated activated βγ part of the G-protein (variant (a)) or with the membrane-bound activated Gα protein subunit which has dissociated off the G-protein (variant (b)) (alternative (ii)) or
  via a "binding" to a membrane-associated molecule which is in a specifically modified state through mediation by the activated βγ part (variant (a)) or the activated Gα protein subunit (variant (b)) of the G-protein (alternative (iii)).

For alternative (i), the effector protein or polypeptide is provided in the cell for example in the form of a fusion protein of an effector section which can bring about activation of the Ras or Ras-like signal pathway with an adaptor protein which interacts with the βγ part of the G-protein after the α subunit has dissociated off (variant (a)) or with the activated Gα protein subunit after dissociation off from the βγ part of the G-protein (variant (b)), in particular with a kinase or a phospholipase C, e.g. a GRK2 or GRK3 kinase (GRK="G-protein coupled receptor kinase") or with a phosphatidylcholine phospholipase C.

An alternative possibility for alternative (i) is for the effector protein or polypeptide also to be provided in the form of a fusion protein of the effector section with an antibody which specifically recognizes the βγ part of the G-protein only after the α subunit has dissociated off (variant (a)) or specifically recognizes the activated Gα protein subunit after dissociation off from the βγ part of the G-protein (variant (b)).

For alternative (ii) it is possible to provide the effector protein or polypeptide inter alia as fusion protein whose adaptor section binds to an adaptor protein with, ordinarily, enzymatic activity, as have been detailed above by way of example specifically for an interaction with G-proteins, the adaptor protein being able to associate or interact specifically with the βγ part of the G-protein only after the α subunit has dissociated off (variant (a)) or with the activated Gα protein subunit only after dissociation off from the βγ part of the G-protein (variant (b)). The adaptor section of the fusion protein may in this connection form, in particular, an antibody or binding protein which specifically recognizes and binds the adaptor protein.

In another case, the adaptor protein also has the property of an antibody or binding protein, in which case the adaptor protein recognizes either specifically the βγ part of the G-protein only after the α subunit has dissociated off (variant (a)) or the activated Gα protein subunit only after dissociation off from the βγ part of the G-protein (variant (b)). In this situation, the adaptor section of the fusion protein usually has in particular the function of a so-called "secondary antibody" or anti-antibody which recognizes the so-called "primary" antibody associated with the mediator section.

For alternative (iii), use is made of the fact that a G-protein in the activated state can activate a phosphatidylinositol 3-kinase (PI3K) which in turn, as a result of the activation, generates so-called second messenger compounds by phosphorylation of the D-3 position of the inositol ring of phosphoinositides (e.g. PtdIns(3,4)P$_2$ (AKT) or PtdIns(3,4,5)P$_3$ (BTK)). These phosphoinositides are membrane-associated and, in their phosphorylated state, bind so-called Src homology (2) (SH2) and pleckstrin homology (PH) domains. For alternative (iii) accordingly the effector protein or polypeptide is provided in a particular embodiment in the form of a fusion protein of the effector section, which is able to bring about activation of the ras or ras-like signal pathway, with an Src homology (2) (SH2) domain or with a pleckstrin homology (PH) domain. The translocation of the effector protein or polypeptide in the form of the effector section accordingly takes place only when phosphorylation takes place to give the specifically mentioned phosphoinositides as a result of G-protein activation, as a result of which the (SH2) or (PH) domains of the fusion protein associate with these phosphoinositides.

Variant c:

As explained, an effector protein or polypeptide translocation onto the membrane can alternatively also take place via the mediator section of the membrane receptor in its specific structure present after binding of a ligand to the ligand-binding section of the membrane receptor or, alternatively, when there is a lack of binding of a ligand to the ligand-binding section of the membrane receptor, specifically through direct "binding" to the mediator section in its specific structure present after binding or only when there is an lack of binding of a ligand to the ligand-binding section of the membrane receptor (alternative (i)) or via one or more adaptor protein(s) which are associated with the mediator section in its specific structure present after binding or only when there is a lack of binding of a ligand to ligand-binding section of the membrane receptor (alternative (ii)).

For alternative (i), the effector protein or polypeptide is provided in the cell for example in the form of a fusion protein of an effector section which is able to bring about activation of the Ras or Ras-like signal pathway with an adaptor protein which interacts with the mediator section of the membrane receptor only in its specific structure present after binding of a ligand to the ligand-binding section of the membrane receptor or, alternatively, only if there is a lack of binding of a ligand to the ligand-binding section of the membrane receptor, in particular an antibody or binding protein of appropriate specificity. For alternative (ii) of this variant, the effector protein or polypeptide can be provided in particular as fusion protein whose adaptor section binds to an adaptor protein which can associate or interact specifically with the mediator section of the membrane receptor only in its specific structure present after binding of a ligand to the ligand-binding section of the membrane receptor or, alternatively, only when there is a lack of binding of a ligand to the ligand-binding section of the membrane receptor. The adaptor section of the fusion protein can in this connection in particular form an antibody or binding protein which specifically recognizes and binds the adaptor protein. In the specific case where the adaptor protein also shows the property of an antibody, in which case the adaptor protein recognizes the mediator section of the membrane receptor specifically only in its specific structure present after binding or only when there is a lack of binding of a ligand to the ligand-binding section of the membrane receptor, the adaptor section of the fusion protein in this situation has the function of a so-called "secondary antibody" or anti-antibody which recognizes the so-called "primary" antibody associated with the mediator section.

2) In a second variant, the receptors chosen for the membrane receptor have mediator sections which, on binding of ligand to the ligand-binding section of the membrane receptor or, alternatively, only when there is a lack of binding of ligand to the ligand-binding section of the membrane receptor, are able to bind adaptor proteins which facilitate the binding of the effector protein or polypeptide.

The membrane receptors suitable for this purpose, which, where appropriate, also provide only the mediator section, are, in particular, enzyme-coupled receptors with intrinsic enzymatic activity and, in particular, with kinase activity, for example tyrosine kinase activity, serine/threonine kinase activity or phosphatase activity, which is localized in the cytoplasmic section of the receptor. The enzymatic activity of the mediator section in this case becomes active only on binding or, alternatively, only when there is a lack of binding of ligand to the ligand-binding domain of the membrane receptor as a result of the structural and, in particular, conformational change brought about by the (lack of) ligand binding. The enzymatic activity is moreover in certain embodiments also necessary for the binding, possible when there is ligand binding or, alternatively, when there is a lack of ligand binding, of the adaptor protein(s) to the mediator section, e.g. via an in some cases multiple phosphorylation of the mediator section (cf. FIGS. 2a and 3) and/or else via a phosphorylation of adaptor protein(s). One example of a corresponding naturally occurring enzyme-coupled receptor is the epidermal growth factor receptor (EFFR), which has tyrosine kinase activity (cf. FIG. 3).

The membrane receptors which can be employed in this case may be, as for 1), naturally occurring receptors, receptors derived from such receptors, or else synthetic receptors which comprise, in particular, sections of diverse origin with the aforementioned functions such as membrane localization, ligand binding and mediator function. These sections may in turn derive from naturally occurring receptors or proteins of other types, or be derived from such according to the criteria already explained. In a specific embodiment of the invention, also with the synthetic receptors of this type the ligand-binding section brings about, on binding of ligand, the structural and, in particular conformational changes which occur naturally with enzyme-coupled receptors in this case and which have an effect on the mediator section and, in particular, on the enzymatic activity localized in this section. However, in this case too, other types of structural changes with effects detectable according to the invention on the mediator section of the receptor and, in particular, on the enzymatic activity localized in this section are also conceivable as an alternative.

An effector protein or polypeptide translocation onto the membrane can now take place by binding of the effector protein or polypeptide to the adaptor protein which is membrane-associated because of binding to the mediator section (alternative (a)) or through use of a fusion protein which contains the effector protein or polypeptide fused to the adaptor protein (alternative (b)).

For alternative (a) it is possible in a particular embodiment to choose mediator sections of membrane receptors which, in the event of binding of ligand to their ligand-binding section or, alternatively, when there is a lack of binding of ligand to their ligand-binding section, bind adaptor proteins to which guanine nucleotide exchange factor (GEF) naturally binds. The epidermal growth factor receptor (EGFR) and the adaptor proteins Grb2 and Shc which are specific for its cytoplasmic or mediator section represent one example of such a membrane receptor. In turn there is binding to these adaptor proteins Gbr2 and Shc, which bind to the mediator section of the EGFR only in the event of ligand binding to the ligand-binding section thereof, by a guanine nucleotide exchange factor which is able to activate a ras or ras-like signal pathway in a cell.

In another embodiment of alternative (a), however, it is possible for the effector protein or polypeptide also to be provided in the form of a fusion protein of an effector section which is able to activate a Ras or Ras-like signal pathway in a cell, and of a section having the property of an antibody or binding protein, and the section having the property of an antibody or binding protein specifically recognizes and binds the adaptor protein(s) which, as a result of ligand binding or, alternatively, because of a lack of ligand binding to the ligand-binding section of the membrane receptor, are bound to the mediator section thereof.

In a specific variant of this embodiment, the adaptor protein is not a naturally occurring adaptor protein such as Grb2 or Shc, or an adaptor protein derived therefrom, but likewise has the property of an antibody, and the antibody adaptor protein, as just explained, recognizes and binds the mediator section of the membrane receptor only as a result of ligand binding to the ligand-binding section or, alternatively, as a result of a lack of ligand binding with a ligand-binding section thereof. In this case, the adaptor section of the fusion protein then has the function of a so-called "secondary antibody" or an anti-antibody which recognizes the so-called "primary" antibody associated with the mediator section.

In alternative (b), the effector protein is provided in the form of a fusion protein which contains the effector section fused to the adaptor protein. Binding of the adaptor protein section of the fusion protein to the mediator section of a membrane receptor as a result of ligand binding or, alternatively, of a lack of ligand binding to the ligand-binding section thereof leads via the covalent linkage within the fusion protein to the effector section also being guided onto the membrane, and it is able to exert its effect there for activation of a Ras or Ras-like signal pathway.

One example of this variant (b) is a fusion protein which comprises as adaptor section a Gbr2 or Shc protein fused to a preferably constitutively active ras protein, for example the human constitutively active ras protein (Haras, L61) or to a functional GEF as effector section. Such a fusion protein is employed, for example, again in conjunction with an EGFR membrane receptor or with a receptor which comprises the cytoplasmic part thereof, in which case the cytoplasmic or mediator section of the EGFR interacts with the Gbr2 or Shc portion of the fusion protein on binding of ligand and thereby guides the effector section onto the membrane (cf. also FIGS. 2a, 3).

Another example of this variant (b) is a fusion protein which has as adaptor section an antibody or a binding protein which recognizes and binds specifically the mediator section of the membrane receptor only in its structure/conformation of the binding of a ligand to the ligand-binding section or, alternatively, when there is a lack of binding of a ligand to the ligand-binding section.

3) The third variant is similar to the second variant but the enzyme-coupled receptor employed as membrane receptor or used to form the mediator section of the membrane receptor does not have intrinsic enzymatic activity activated on ligand binding or, alternatively, when there is a lack of ligand binding but, on the contrary, activates, strictly dependent on its own activation by ligand binding or lack of ligand binding, a separate receptor-specific enzyme which is located, for example, on a separate subunit. Various cytokine receptors can be mentioned as examples of such a receptor type.

This separate receptor-specific enzyme may also, in a particular embodiment, be heterologous to the cell. The separate receptor-specific enzyme is preferably likewise a kinase and, in particular, a tyrosine kinase. Once again, the kinase activity preferably leads to phosphorylation of the mediator section, i.e. the cytoplasmic section of the membrane receptor and thus has an additional effect on the binding of an adaptor protein specific for the mediator section.

Otherwise, the same applies as for the membrane receptor of variant 2) i.e. the latter can be a naturally occurring membrane receptor, a membrane receptor derived from such a membrane receptor, or a synthetic membrane receptor whose various domains or sections originate from different sources which, where appropriate, may also be derived from naturally occurring sequences.

As with variant 2), it is also possible in this case for the effector protein or polypeptide translocation onto the membrane to take place through binding of the effector protein or polypeptide to an adaptor protein which is membrane-associated because of binding to the mediator section (alternative (a)) or by use of a fusion protein which contains the effector protein or polypeptide fused to the adaptor protein (alternative (b)).

It is also possible in this case to mention Grb2 or Shc as examples of possible adaptor proteins which can be employed, where appropriate also as fusion proteins with an effector section which is able to activate the Ras or Ras-like signal pathway, but also antibodies or other types of binding proteins which recognize and bind specifically the mediator section of the membrane receptor only in its structure/conformation after binding of a ligand to the ligand-binding section or, alternatively, only when there is a lack of binding of a ligand to the ligand-binding section, and can be employed in the form of fusion proteins with an effector section. Alternatively, the antibody adaptor protein or binding protein adaptor protein comprises no effector function but is in turn recognized and bound by a fusion protein with an effector section and an adaptor section with the function in particular of a so-called "secondary antibody" or anti-antibody which recognizes the so-called "primary" antibody (antibody adaptor protein) associated with the mediator section, via this adaptor section.

4) In another, fourth variant, the membrane receptor employed is a fusion protein which has within its sequence, in particular at or in the region of the C terminus, a so-called tag or epitope which is accessible for recognition by an antibody specific therefor or a binding protein specific therefor only on binding of ligand to the ligand-binding section, or alternatively, only when there is a lack of binding of ligand to the ligand-binding section. Examples of suitable tags or epitopes which can be mentioned are a Myc tag, His tag, hemagglutinin epitope and the like.

The tag or the epitope may be a part of the mediator section but may also be adjacent thereto or separated therefrom by an amino acid sequence section. However, the accessibility thereof is made possible for a specific antibody or a specific binding protein only because of conformational changes, where appropriate in combination with enzymatic activity, as a result of binding of ligand to the ligand-binding section of the membrane receptor or, alternatively, because of dissociation of ligand off from the ligand-binding section of the membrane receptor, i.e. in the latter variant when there is a lack of ligand binding. A tag or epitope can thus be attached to all the receptor types mentioned, that is to say a G-protein-coupled receptor (GPCR) as well as to receptor tyrosine kinases or receptor phosphatases, provided that the criteria explained above concerning the accessibility of the tag or epitope are met for an antibody or a specific binding protein.

The effector protein is in this case provided as fusion protein which comprises the effector section and an antibody specific for the tag or the epitope, or a binding protein specific for the tag or the epitope. If the tag or the epitope becomes accessible as a result of ligand binding to the ligand-binding section or, alternatively, as a result of a lack of ligand binding and effects resulting therefrom on the mediator section for the antibody present in the fusion protein or the binding protein present in the fusion protein, the effector protein or polypeptide is translocated onto the membrane through the tag/epitope-antibody/binding protein reaction.

Thus, when the explained conformational preconditions are met, this fourth variant can be employed most widely because it does not otherwise have to take account of the specific requirements of naturally occurring mediator sections such as those of G-protein-coupled receptors, receptor tyrosine kinases or receptor phosphatases, or synthetic mediator sections derived therefrom. In addition, the necessity to provide as effector protein only a fusion protein with effector section and antibody or binding protein sections specific for the tag or epitope brings about a considerable simplification in the method for preparing cells of the invention and of the assay methods which are described in detail hereinafter and which make use of these cells.

If it is intended to carry out with the aid of the described cells the assays of the invention which, as explained in detail hereinafter, specifically detect the interaction of ligands with the ligand-binding section of membrane receptors, it is self-evident that the event of translocation of the effector protein or polypeptide onto the cell membrane must occur only if there is a ligand—ligand-binding section interaction or, alternatively, if there is a lack of a ligand—ligand-binding section interaction on the membrane receptor specifically to be investigated. This means that association of the effector protein or polypeptide with membrane-associated cell components which (in the absence of the membrane receptor and of the cell components cooperating specifically and exclusively with the latter for signal transduction) naturally occur in these cells must be precluded irrespective of the activation or modification state of the cell components, generally or when certain particular cultivation conditions are chosen for the cells. The precondition for this is that all components directly and indirectly involved in the translocation of the effector protein or polypeptide onto the cell membrane can, generally or when these particular cultivation conditions are chosen, only as a result of the activation of the membrane receptor specifically to be tested, because of the binding of a ligand to the ligand-binding section or, alternatively, because of the lack of ligand binding to the ligand-binding section, and more accurately only as a result of the structural change in the mediator section caused by this activation, be made able to mediate or bring about the binding of the effector protein or polypeptide to a component of the cell membrane.

If it is intended to test a membrane receptor naturally occurring in a cell in a test, it must be ensured that the mediator section of this membrane receptor occurs in the cell only in conjunction with the latter and that the adaptor and facilitator proteins cooperating therewith can interact only with this mediator section or only because of activation of this mediator section in such a way that translocation of the effector protein or polypeptide onto the cell membrane eventually occurs.

An alternative possibility is for a cell to be selected as assay cell in which, before introduction of the genetic information for the membrane receptor and the adaptor, facilitator and/or effector proteins or polypeptides which are required where appropriate, none of these components naturally occurs, that is to say are heterologous to this initial cell, and no components of the same specificity and, where appropriate, activity which might replace the latter are intrinsically present in the cell either; in relation to the membrane receptor, this may also apply only to the mediator section. Or care must be taken that an initial cell which in an original state once contained these components, in relation to the membrane receptor where appropriate also only the specific mediator section, no longer contains these components because of genetic or other modification before introduction of the genetic information for the membrane receptor and the adaptor, facilitator and/or effector proteins or polypeptides which are required where appropriate. Explained comprehensively, this relates at least to the following components:

the mediator section, where appropriate the adaptor proteins or adaptor protein sections cooperating therewith where binding of the effector protein or polypeptide takes place to the latter or via the latter, and for example in the case of alternative 1)c) explained herein, where appropriate a facilitator component which need not be directly spatially associated with the mediator section of the membrane receptor but is, in the event of ligand binding or, alternatively, lack of ligand binding to the ligand-binding section, activated or modified by the latter and, for this reason, facilitates a secondary event on another component of the cell membrane, as a result of which the effector protein or polypeptide specifically binds to this component of the cell membrane, which is not associated with the mediator section of the membrane receptor; alternatively, said secondary event in the cell may be facilitated only if there is ligand binding or, alternatively, lack of ligand binding of the ligand-binding section of the membrane receptor. Thus, in the latter case, no interaction partners for these facilitators which are able to exert an activation effect corresponding to the membrane receptor on the facilitator(s) must be present in the cell.

Accordingly, in some embodiments of the invention, the expression of certain types of proteins and fusion proteins in a suitable cell system which does not naturally contain these proteins and fusion proteins is an essential aspect. Depending on the membrane receptor employed and, in particular, depending on the mechanism which is determined by the mediator section of the membrane receptor and which eventually leads to translocation of the effector protein or polypeptide onto the membrane, it may be necessary to express one or more or the aforementioned proteins in a cell which does not naturally contain the latter. These proteins can be expressed in their naturally occurring form, if there is one such, or in the form of fusion proteins.

It is possible in this connection for the gene constructs which encoded these proteins or fusion proteins to be present in the cell chromosomally, i.e. integrated into the chromosome, or extrachromosomally, as constituent of an episome, in particular plasmid.

A first fusion protein of this type may be a membrane receptor as explained above, with which in particular and, where appropriate, also exclusively the mediator section is heterologous to the cell.

Another one of these fusion proteins provides the effector protein or polypeptide in a particular form and consists of domains or parts which combine the following functions:

i) the membrane-associated specific interaction of an adaptor section of the fusion protein with a component of the membrane and, in a particular embodiment, with the mediator section of the receptor as a function of the extracellular ligand binding or, alternatively, of the lack of extracellular ligand binding (adaptor function);

ii) the possibility of activating a ras or ras-like signal transduction pathway as a function of the membrane localization determined by the adaptor section on the basis of an effector section fused to the adaptor section in the fusion protein (effector function).

The former function has the effect that the adaptor-effector fusion protein reaches the membrane and thus the site of action of that part of the fusion protein which is responsible for the second function only when a ligand has bound to the usually extracellular part, i.e. the ligand-binding section, of the receptor or, alternatively, when no such ligand binding is present.

In the former case, the receptor without ligand binding is present in a configuration which is unable to bind the adaptor section directly, or is unable to induce a membrane-associated subsequent process via a mediator which the adaptor section would be able to recognize. In the case of ligand binding, the cytosolic part of the receptor in this variant then assumes a configuration which the adaptor part is able to recognize directly, or it induces a subsequent process leading to a membrane-associated protein configuration of other mediator proteins which the adaptor is able to recognize. Thus, in the absence of ligand binding, the adaptor-effector fusion protein in the cytosol is not present at the site of action of the effector section. Only when the effector section is in a membrane-associated orientation can it act as signal transduction component in the ras or ras-like signal transduction pathway (FIGS. 2a and b).

In the latter case, the receptor is, when there is binding of ligand, present in a configuration which is unable to bind directly the adaptor section or is unable to induce a membrane-associated subsequent process via a mediator which the adaptor section would be able to recognize. When the ligand dissociates off, or if ligand binding is lacking, the cytosolic part of the receptor in this variant then assumes a configuration which the adaptor part is able to recognize directly, or it induces a subsequent process which leads to a membrane-associated protein configuration of other mediator proteins which the adaptor is able to recognize. Thus, in this variant, the adaptor-effector fusion protein is not present at the site of action of the effector section in the cytosol when there is ligand binding. Only when the effector section is in a membrane-associated orientation can it act as signal transduction component in the ras or ras-like signal transduction pathway.

Such an activation can, as explained in more detail hereinafter, be detected from phenotypical changes (e.g. growth or gene or reporter gene activity) in the cell, it being necessary in the first variant for the cells to be inactive in relation to the ras or ras-like signal transduction pathway under the assay conditions in the absence of the ligand, and it being necessary in the latter variant for them to be inactive in relation to the ras or ras-like signal transduction pathway under the assay conditions in the presence of the ligand.

In an experimental system of the invention which is preferably used, the fusion protein comprises as effector section a mutated human Ras protein (Ha-Ras, L61) which lacks the farnesylation sequence which ensures membrane localization of the protein.

It is also possible for other protein components which, besides the membrane receptor and, in particular, its mediator section and the effector protein, are themselves involved in the translocation of the effector protein or polypeptide directly or indirectly to be expressed where appropriate as the fusion proteins which do not occur naturally in the cell.

It may be added, for clearer understanding of the teaching of these documents, that the term "ligand" is intended to mean in the present context only those binding partners for receptors and, in particular, membrane receptors which elicit on binding to the ligand-binding section of such a receptor a structural change, in particular a conformational change and/or an enzymatic modification, e.g. by phosphorylation or dephosphorylation, whose effects on the mediator section result in an effector protein or polypeptide which is able to activate a Ras or Ras-like signal pathway in the cell binding to a component of the membrane, where appropriate via other proteins or polypeptides (adaptors). This may comprise, in particular, structural and, specifically, conformational changes which take place in vivo on binding of a natural ligand and examples of which have been explained above. However, consideration is also given to cases in which the structural and, specifically, conformational change does not correspond, or corresponds only partially, to the structural or conformational change taking place on binding of a ligand which occurs in vivo in the cell. Binding partners which do not elicit such a structural change are not embraced by the term "ligand".

The terms "Ras and Ras-like signal pathway" or "signal pathway subsequent to a Ras protein", used synonymously herein, also embrace the so-called ras-like signal pathways which are controlled by various other members of the Ras family. Among the members of the Ras family there are ones which, despite originating from different organisms, are able to activate one and the same signal transduction pathway in the chosen target cell. One example thereof is the human Ha-Ras (L61) which is able also to activate a ras signal pathway in *Saccharomyces cerevisiae* which acts on the cell cycle and whose activation is essential for reproduction of yeast cells. Other members of the Ras family are able only to activate a single signal pathway specific for them.

A number of members of the Ras family, such as the aforementioned Ha-Ras (L61), activates signal pathways which act on the cell cycle and whose activation are essential for cell reproduction via activation of specific transcription factors. Other Ras proteins of this type activate signal pathways which specifically lead to activation in each case of one of a multiplicity of transcription factors which are specific for genes other than those of the cell cycle. In the present context, a common feature of all ras signal pathways is that they require for their activation an active Ras protein present on the cell membrane, and the Ras protein requires for its activity where appropriate the simultaneous presence of a guanine nucleotide exchange factor on the cell membrane.

Reference in these documents to an inactivation of a ras signal pathway or of a ras-like signal pathway always means an inactivation of a level of the ras protein and/or of a guanine nucleotide exchange factor specific therefor. Said signal pathway inactivation occurs in a cell in the present context preferably only under certain environmental conditions, such as temperature, and can thus be induced and abolished again by specific adjustment of environmental conditions.

In the cellular context, a ras or ras-like signal transduction pathway is activated in each of the explained embodiments by the action of the active signal transduction components. Use of a cell in which this ras or ras-like signal pathway is not activated in the absence of the membrane receptor indicated according to the invention, because of mutations, at least under certain conditions, it is possible to detect one such solely by the activation mediated [lacuna] the translocation, resulting from the ligand binding or, alternatively, resulting from the lack of ligand binding to precisely this membrane receptor, of the effector protein or polypeptide onto the cell membrane, via phenotypical changes, e.g. growth or gene or reporter gene activity, in the cell.

The effector protein or polypeptide is preferably able to activate ras signal transduction pathways which act on the cell cycle and whose activation is essential for cell reproduction. Alternatively and likewise preferably it acts on one of the Ras signal pathways which serves to activate transcription factors for genes which need not be essential for cell reproduction.

The effector protein or polypeptide may have the activity of an active and, in particular, of a constitutively active Ras protein. Constitutively active Ras proteins show activity irrespective of the presence of guanine nucleotide exchange factor molecules, which various other Ras proteins require for their activity. For this purpose, the effector protein or polypeptide may comprise, for example, the amino acid sequence of an active or constitutively active Ras protein which occurs in nature, e.g. the human Ha-Ras (L61), or of parts thereof. Or it may comprise amino acid sequences which are derived from such sequences, for example by attachment, exchange, modification, insertion or deletion of amino acids.

An alternative possibility is for the effector protein or polypeptide to house the activity of a functional guanine nucleotide exchange factor. In this respect, the amino acid sequence of the effector protein or polypeptide may likewise comprise, for example, sequences of naturally occurring guanine nucleotide exchange factors or partial sequences thereof, or it may be derived therefrom, for example by attachment, exchange, modification, insertion or deletion of amino acids. In a preferred embodiment, the amino acid sequence of the effector protein or polypeptide is derived from the amino acid sequence of the CDC25 protein from *Saccharomyces cerevisiae*, of an SOS protein from a mammal or of an SOS-like protein derived from any organism.

In addition, the invention comprises DNA molecules which encode novel fusion proteins, to which the invention likewise relates, and vectors, in particular plasmids, cosmids, viral or phage genomes, which comprise at least one of these DNA molecules. Particular vectors of the invention are suitable for the transformation or transfection of host cells or for the expression of at least one fusion protein of the invention. For the latter purpose, a DNA molecule of the invention in the vector is under the control of a promoter which is capable of functioning in a host cell and which makes expression possible and controls it.

Preparation of the fusion proteins, DNA molecules and vectors of the invention can take place by protocols known in the prior art (see, for example, Sambrook, J., Fritsch, E. F., Maniatis, T. (1989), Molecular Cloning. A Laboratory Handbook, Cold Spring Harbor Laboratory, New York; Current Protocols in Molecular Biology (1991)). Even if the fusion proteins can in principle be prepared by complete synthesis from individual amino derivatives, for which various methods are available in the prior art, they are normally produced by expression of the appropriate genes in cells. In this case, the gene for the fusion protein may be present extrachromasomally or integrated into the genome of the host cell. The cloning of the genes for the fusion proteins starting from known gene sections which encode protein sections with the necessary functions or else, in the case of the ligand-binding or receptor section, at present only presumed functions likewise form as part of the standard abilities of a skilled worker, such as the construction of vectors, such as transcription or transfection vectors or else expression vectors, in which the gene is present functionally linked to a promoter effective in the producing cell, the transformation or transfection of host cells as well as the cultivation of the transformed or transfected host cells for producing the protein. The isolation and purification of the fusion proteins of the invention can take place through use of conventional methods such as precipitation, use of various chromatographic methods such as gel filtration, affinity chromatography etc. Affinity chromatography in particular allows selective binding only of the fusion protein, for example on use of specific antibodies or binding proteins which are bound to the matrix and which are directed against a determinant of a section, which is heterologous in relation to the host cell, of the fusion protein. An alternative possibility is for the fusion protein to be expressed, for example, also as precursor protein which has an additional domain with a specific property of binding to a particular affinity column. After binding and subsequent elution from the affinity column it is then possible for the additional domain to be eliminated selectively from the precursor protein, which is now already in essentially pure form, to produce the fusion protein of the invention. However, where the additional domain has no effect on the suitability of the fusion protein for the assay of the invention, it is also possible alternatively to dispense with the elimination step. One example of such a domain consists of a plurality of, for example 10, histidine residues additionally attached at the N terminus ("His tag") and specifically binding to a metal chelate affinity chromatography column. Concerning all the techniques mentioned and the reagents necessary therefor, including vector molecules, reference may be made to standard literature (e.g. Sambrook, J., Fritsch, E. F., Maniatis, T. (1989), loc. cit.; Current Protocols in Molecular Biology (1991)) and an immense number of individual protocols.

Another central aspect of the invention besides the cells explained above are also cells which comprise one or more of the membrane receptors as described in claim 1, in particular one or more of the membrane receptor fusion proteins of the invention. Within the framework of this invention it is moreover possible for single, a plurality of or else all domains of the membrane receptor/fusion protein and/or where appropriate also parts of one or more sections or domains of the latter to be heterologous in relation to the host or initial cell.

To prepare the cells of the invention it is possible, for example, to transform or transfect initial cells with an expression vector which contains a gene for a membrane receptor with the features explained in claim 1, in particular a fusion protein of the invention under control of a promoter capable of functioning in the initial cell. Suitable initial cells are prokaryotic as well as eukaryotic cells. Examples of initial cells are, inter alia, bacterial cells, such as those of the genus *Escherichia* or *Bacillus*, for example certain strains of *Escherichia coli* or *Bacilluls subtilis*, yeast cells, such as certain strains *Saccharomyces cerevisiae*, insect cells, animal cells such as COS-7, vero, CHO cells, mouse myeloma cells, human FL cells etc.

The cells can also be provided in the form of ghost forms of the yeasts lacking cell walls, which are likewise embraced by the term "cells" in the present context.

An essential feature of the cells of the invention is that, when there is a lack of binding of ligand to the ligand-binding section of the membrane receptor, the effector protein or polypeptide is not able to bring about the activation of the specific Ras or Ras-like signal pathway in the cells or, alternatively, that the effector protein or polypeptide is not able, specifically when there is ligand binding to the ligand-binding section of the membrane receptor, to bring about the activation of the specific Ras or Ras-like signal pathway in the cells.

In a preferred embodiment of this invention, the cell of the invention is characterized in that, in the absence of the membrane receptor set forth in claim 1, at least under certain conditions a Ras or Ras-like signal pathway in the cell cannot be activated and, in particular, the signal pathway which the effector protein or polypeptide is able to activate. Thus, cells in which a particular ras signal transduction pathway is active or inactive depending on the temperature are known in the prior art. Cells of this type can be employed as initial cells for expression of the fusion protein or membrane receptor of the invention.

The inactivation, which is present at least under certain conditions, of a ras signal transduction pathway results from a Ras protein and/or guanine nucleotide exchange vector which is incapable of functioning at least under the particular conditions. The inactivation may derive from genetic mutation or complete or partial gene deletion. For example, a Ras protein intrinsic to a cell can be inactivated when its membrane-localization signal, usually a farnesylation signal, is deleted. A mutation in this membrane-localization signal with the effect that binding of the Ras protein to the cellular membranes can no longer take place would have the same effect. One example of a cell with a temperature-dependently defective guanine nucleotide exchange factor is the *Saccharomyces cerevisiae* yeast strain cdc25-2 (Broder et al., 1998). In this strain the guanine nucleotide exchange factor is no longer active at a restrictive temperature of 33 to 37° C., typically 36° C., but is fully capable of functioning at a temperature of, for example, 25° C. Since the guanine nucleotide exchange factor cooperates in this yeast strain with a Ras protein which controls a ras signal transduction pathway which acts on the cell cycle and is therefore essential for cell growth, no reproduction of the cells of the yeast strain is detectable at a restrictive temperature.

In a manner analogous to yeast strains with a temperature-sensitive mutation of an SOS protein intrinsic to yeast (CDC25-2) it is also possible to employ a yeast strain with a temperature-sensitive mutation of a Ras protein intrinsic to yeast.

An alternative possibility for preparing the cells of the invention is, however, also to use a cell, i.e. yeast cell or mammalian cell, which is in fact able to express a wild-type or mutated but active CDC25/SOS protein or Ras protein, but in which the gene encoding this active CDC25/SOS protein or Ras protein is under the control of an inducible promoter through which expression of the gene can be switched on or off deliberately by choosing particular culturing conditions. Examples of inducible promoters which can be employed in this connection are the galactose promoter or parts thereof from yeast or other organisms. The skilled worker is aware of a large number of inducible promoters suitable for this purpose from a wide variety of organisms. It is also possible to employ hybrid promoters with suitable inducibility.

If the cell of the invention expresses an active CDC25/SOS protein or an active Ras protein, it is possible in another preferred embodiment of the invention for the CDC25/SOS or Ras protein additionally to contain a modification through which the protein degradation in the cell is speeded up. This modification may be, for example, a ubiquitin signal or another signal which ensures the preferred degradation of a protein modified in this way in the cell. The advantage of expressing a protein modified in this way during induction of the promoter is that degradation of the CDC25/SOS or Ras protein produced at the time of induction of the promoter is speeded up after "switching off" of the promoter, i.e. after providing culturing conditions with which the promoter is not induced and accordingly there is no longer any transcription of the CDC25/SOS or Ras gene. Accordingly, even a short time after "switching off" of the promoter it is no longer possible to detect any such active CDC25/SOS or ras protein in the cell. In the preferred situation where the mediator section of the membrane receptor investigated according to the invention is able, via its effect on the effector protein or polypeptide, precisely to activate the signal pathway which is activated by the active CDC25/SOS or ras protein mentioned above, it is thus possible even a short time after changing the culturing conditions to switch off the promoter for the activation of this signal pathway to be measured exclusively on the basis of the effects of the membrane receptor investigated according to the invention, which may signify a considerable advantage in terms of time. It is additionally possible in this way to reduce significantly the background signal based on an activation, which is possibly still present to a small extent and is not attributable to the membrane receptor investigated according to the invention, of the signal pathway.

If the inactivation or inactivatability of the ras signal transduction pathway intrinsic to the cell is based on a defect or absence of a guanine nucleotide exchange factor, it is possible in the preferred case where the effector protein or polypeptide is able to activate precisely this ras-signal transduction pathway for this effector protein or polypeptide to have the activity of a functional guanine nucleotide exchange factor or of an active, in particular constitutively active, Ras protein, each of which is able to activate the inactive ras signal transduction pathway. If an effector protein or polypeptide with an activity of a non-constitutively active Ras protein is employed, it is reasonable for it to have the following properties: it requires activation by a different type of guanine nucleotide exchange factor which is unable to interact functionally with the Ras protein, intrinsic to the cell, of the inactive ras signal transduction pathway. It is possible where appropriate for this specifically suitable guanine nucleotide exchange factor to be coexpressed as heterologous factor in the cell or assay cell of the invention.

If the inactivation or inactivatability of the ras signal pathway intrinsic to the cell is attributable to a defect or absence of a Ras protein intrinsic to the cell, then in the preferred case where the effector protein or polypeptide is able to activate precisely this ras signal pathway the latter will have the activity of an active, in particular constitutively active, Ras protein. If the effector protein or polypeptide has the activity of a non-constitutively active Ras protein, then activation thereof preferably takes place through a guanine nucleotide exchange factor intrinsic to the cell, but, as an alternative to this, it may also require a heterologous guanine nucleotide exchange factor to be coexpressed in the cell.

The techniques of molecular biology necessary for preparing the cells of the invention, e.g. cloning, vector construction, transformation or transfection, selection of transformed or transfected cells and calculation of the transformed or transfected cells etc., are well known to the skilled worker, and many general protocols exist for these purposes and may where appropriate require slight adaptation, see, for example, Sambrook, J., Fritsch, E. F., Maniatis, T. (1989), loc. cit.; Current Protocols in Molecular Biology (1991) and numerous protocols specifically drawn up for a particular cell type. The expression of, for example, heterologous proteins and fusion proteins may moreover, as mentioned, take place starting from a gene present extrachromosomally within an episome, in particular plasmid, and take place starting from a gene integrated into the genome of the initial cell. Various techniques are available to the skilled worker for producing cells in which a particular ras signal transduction pathway is inactivated at the level of the Ras protein and/or of a guanine nucleotide exchange factor and, in particular, for specific gene inactivation which may also be necessary in another connection for certain assay situations, for example through antisense strategies or for targeted introduction of mutations or deletions in the particular genes or relevant genome sections. In particular, there are various known possibilities for preparing cell mutants in which transcription of the genes for example for the Ras protein or a guanine nucleotide exchange factor can be inactivated deliberately under certain conditions, e.g. temperature-dependently. For this purpose, these cells contain these genes in particular linked to promoters which become inactive under certain conditions, such as starting at a particular temperature.

In a particular embodiment of the invention, the cells and assay cells of the invention are applied to a solid carrier. Suitable carrier substances known in the prior art are, in particular, polysaccharides, e.g. agarose, specific plastics such as polyacrylamides, polystyrene, polyvinyl alcohol, silicones, or else certain types of glass. The carrier may in this case be in the form of separate particles, for example beads, or of an essentially plate-like substrate, e.g. in the form of a microtiter plate. The covering of the carrier with the cells may be complete, as is usually the case for example with carrier beads, or else present on only parts or sections thereof, such as, for example only in the wells of a microtiter plate. In a preferred embodiment, the cells of the invention are immobilized on so-called biochips (Wolf et al. 1997 and 1998). Immobilized on a solid carrier and, in particular, biochips, the cells are employed in this form in particular in high-thoughput methods for detecting and measuring membrane receptor-ligand interactions. Methods for immobilizing the cells on these carriers are known to the skilled worker. It is possible, depending on the chosen carrier type, for the cells to bind to the carrier without further measures. In this case, the solid carrier phase is incubated with an essentially homogeneous population of cells, resulting in adhesion thereof to the solid phase. An alternative possibility is for the immobilization also to take place for example by means of chemical reagents such as glutaraldehyde, formalin etc. Measures of these types are known to the skilled worker.

The cells and fusion proteins of the invention are the basis for a number of in vivo assay methods, to which this invention likewise relates.

The assay methods which can be implemented using the first variant, i.e. effector protein or polypeptide translocation onto the cell membrane possible only when there is ligand binding to the ligand-binding section of the membrane receptor investigated according to the invention, and which are explained in detail hereinafter can be used, inter alia 1. to determine the suitability of a test substance as ligand for a receptor and, in this case, in particular to carry out mass screens with ligand derivatives in order to test which derivatives are able to bind to the wild-type ligand-binding section of the receptor,
2. to detect the presence of a particular ligand in a sample,
3. to determine the concentration of such a ligand in a sample,
4. to detect whether a compound is able to alter a binding activity of a ligand-binding section of a receptor in relation to a ligand, that is to say to act as agonist, antagonist or inhibitor, and in this case in particular to carry out mass screens for finding such agonistic or antagonistic compounds; and
5. to detect the ligand-binding function of a polypeptide or protein suspected of having such a function for ligands of particular receptors; the polypeptides or proteins may be, in particular, novel ligand-binding sections, derived from natural receptors by mutation, of receptors whose ligand-binding function still needs confirmation; in this connection it is possible in particular to carry out mass screens with such novel, mutated ligand-binding sections which [lacuna] for example in the form of a receptor mutant library which contains, in particular, receptor mutants with randomly localized mutations in the ligand-binding section, in order to find novel artificial, functional ligand-receptor partners.

A first assay is used to determine the suitability of a test substance as ligand for a receptor section or, synonomously, ligand-binding section of a receptor and comprises the following steps:

(a) contacting the test substance with cells of the invention under conditions with which a Ras or Ras-like signal pathway cannot be activated in the cells in the absence of the membrane receptor, where the membrane receptor present in the cells contains said ligand-binding section, and the effector protein or polypeptide whose binding to a membrane component depends on the binding of a ligand to the ligand-binding section of the membrane receptor is able to activate the inactive Ras or Ras-like signal pathway, (b) investigating whether activation of the Ras or Ras-like signal pathway has taken place.

Detection of the activation of the Ras or Ras-like signal pathway indicates in this case the ability of the test substance to bind to the ligand-binding section.

Another in vivo assay makes it possible to detect the presence of a ligand for a ligand-binding section of a receptor in a sample which possibly contains the latter, and is characterized by the following steps:

(a) contacting the test substance with cells of the invention under conditions with which a Ras or Ras-like signal pathway cannot be activated in the cells in the absence of the membrane receptor, where the membrane receptor present in the cells contains said ligand-binding section, and the effector protein or polypeptide whose binding to a membrane component depends on the binding of a ligand to the ligand-binding section of the membrane receptor is able to activate the inactive Ras or Ras-like signal pathway, (b) investigating whether activation of the Ras or Ras-like signal pathway has taken place.

In analogy to the former assay, detection of the activation of the Ras or Ras-like signal pathway indicates the presence of a ligand for the ligand-binding section of a receptor in the sample.

Preferred Ras or Ras-like signal pathways, which are referred to hereinafter alternatively also as only Ras signal pathways, are regarded in this connection as being, as explained, signal pathways which act on the cell cycle and whose activation is essential for cell reproduction. Alternative and equally preferred ras signal pathways serve to activate transcription factors for genes which need not be essential for cell reproduction.

Detection of Ras signal pathway activation thus preferably takes place in the assays of the invention indirectly, i.e. via phenotypical changes, in this case in particular cell reproduction or gene or reporter gene activity, in the cells.

If, accordingly, the cells employed for the assays are ones in which the inactive Ras or Ras-like is a signal pathway which acts on the cell cycle and whose activation is essential for cell reproduction, the steps (b) explained above for investigating whether the cells are capable of reproduction under the conditions mentioned comprise, and detection of the ability of the cells to reproduce indicates the ability of the test substance to bind to or the presence of a ligand for the ligand-binding section of the membrane receptor in the sample.

If, alternatively, the cells employed for the assays are those in which the inactive Ras or Ras-like signal pathway is a signal pathway which acts on the activity of a transcription factor for a gene which is not necessarily essential for cell reproduction, it is possible in the simultaneous presence of a construct comprising a binding site for the transcription factor, a minimal promoter cooperating therewith and a gene, under the control of the minimal promoter, for a reporter protein, to use detection of expression of the reporter gene through detection of the transcription or translation products thereof for establishing the activation of the ras signal transduction pathway and thus that ligand binding has taken place on the ligand-binding section of the membrane receptor. This is because only on activation of the ras signal transduction pathway is it possible for there to be activation of said transcription factor, which is subsequently able to activate, via binding to its binding site, the minimal promoter and thus makes expression of the reporter gene possible.

In a preferred embodiment, the reporter gene or protein is a gene or protein which is heterologous in relation to the assay cell and whose presence can be specifically detected only when expression of the synthetic promoter-reporter gene construct takes place because of activation of the specific ras signal pathway and the resulting activation of the specific transcription factor. If detection takes place not as direct detection of the transcription or translation product by means of nucleic acid probes or antibodies specific therefor, but takes place, for example, via the enzymatic activity of the translation product, it is necessary on use of enzyme-encoding genes to ensure beforehand that the assay cell used does not, before the transformation or transfection with the synthetic promoter-reporter gene construct, contain an enzymatic activity like that of the heterologous enzyme expressed on ligand binding. A corresponding statement applies to the other types of reporter protein.

An alternative possibility is also to employ a gene which is homologous in relation to the assay as reporter gene. Reporter gene expression as a result of a transcription factor activation which takes place only because of the activation, to be detected in the assay, of a Ras or Ras-like signal pathway in the cells will in this case lead to an increase in the amounts of reporter gene transcription product present in the cells and, where appropriate, also an increased amount of the report gene translation product, and these can be measured by means of comparative experiments without use of ligands, e.g. by Northern blotting or Western blotting.

If these two latter alternatives are chosen, it is necessary to know the particular transcription factor activated by the chosen ras signal transduction pathway, and the promoter section, or its sequence, cooperating with this transcription factor. In order to make this assay variant possible, the assay cell will be transformed or transfected with a construct comprising the promoter functionally linked to the reporter gene, which can, where appropriate, take place by cotransformation or cotransfection together with one or more construct(s) which contain genes for other components of the assay system, e.g. the membrane receptor.

As mentioned, these constructs may, after transformation or transfection of an initial cell, be present chromosomally or extrachromosomally, i.e. as constituent of an episome, e.g. plasmid, in the assay cell.

At present, a number of ras signal transduction pathways, e.g. in different eukaryotic organisms, have already been completely researched in relation to the transcription factors activated thereby and the promoter regions cooperating therewith. A number of possibilities is thus available to the skilled worker for a selection in this regard.

In a preferred embodiment of the invention, the reporter protein comprises a modification which results in faster breakdown or degradation of the protein in the cell. This modification may be, for example, a ubiquitin signal or other signal which ensures breakdown of a protein modified in this way. The advantage of the use of a reporter protein which is broken down faster in an assay cell is obvious in the light of fact that a low background expression of the reporter gene construct will virtually always be detectable under the assay conditions, even without activation of the Ras or Ras-like signal pathway through the membrane receptor in the assay cell: the fast breakdown of the reporter protein significantly reduces the signal resulting from this background expression on detection of the protein level, i.e. of the reporter protein, because there is no accumulation of reporter protein over time. If, however, expression of the reporter protein is specifically activated by ligand binding to the membrane receptor and, resulting therefrom, activation of a Ras or Ras-like signal pathway, unambiguous detection is possible because the background signal is low. Since the half-life of the reporter protein in the assay cell will always be sufficiently long, detection of the reporter protein, produced as a result of ligand binding to the membrane receptor, will not be impaired in any way through the fast breakdown thereof.

The molecular biology techniques necessary for the preparation of transformation or expression vectors which contain the reporter gene functionally linked to a suitable specific promoter, and the transformation or transfection of cells, e.g. cloning, vector construction etc., are well known to the skilled worker and numerous general protocols exist therefor and require, where appropriate, at most slight adaptation (see, for example, Sambrook, J., Fritsch, E. F., Maniatis, T. (1989) loc. cit.; Current Protocols in Molecular Biology (1991)). The addition or fusion to a reporter gene of a sequence section which encodes a signal section which brings about faster breakdown of the expressed reporter protein, e.g. a ubiquitin signal, is well within the capacity of a skilled worker.

The skilled worker is aware of numerous genes which can be employed as reporter genes in this connection and which encode proteins which are amenable to simple and rapid detection. Examples thereof are genes which encode enzymatically active proteins, e.g. β-galactosidase, fluorescent proteins, e.g. GFP (green fluorescence protein) or chemoluminescent proteins. Another possibility comprises genes which encode proteins which can be detected using specific antibodies. In this case, the antibody carries a detectable label or can in turn be detected by a secondary, labeled antibody. Possibilities of these types are well known in the prior art. As already explained above, besides the necessity for detectability, it is essential only that the event to be detected in the cell, e.g. enzymatic activity, antibody binding, fluorescence, chemoluminescence, is undetectable in the absence of the construct with the gene for the reporter protein.

An alternative possibility is for the transcription of the reporter gene to be detected on the basis of the mRNA formed, by Northern blotting using probes specific therefor.

Another in vivo assay permits quantitative determination of the concentration of a ligand for a ligand-binding section of a receptor in a sample which contains the latter, characterized by the following steps:
  (a) contacting an aliquot of the sample with cells of the invention under conditions with which, in the absence of the membrane receptor, a Ras or Ras-like signal pathway in the cell cannot be activated, where the membrane receptor contains said ligand-binding section, and the effector protein or polypeptide whose binding to a membrane component depends on the binding of a ligand to the ligand-binding section of the membrane receptor, as defined in Claim 1, is able to activate the inactive Ras or Ras-like signal pathway,
  (b) detecting quantitatively the extent of the activation of the Ras or Ras-like signal pathway by direct or indirect means,
  (c) measuring the concentration of the ligand in the sample by comparing the measured extent of activation with corresponding values measured for known standard concentrations of the ligand.

If cells for which the ras signal transduction pathway which is inactive at least under certain conditions is a signal pathway which acts on the cell cycle and whose activation is essential for cell reproduction are used for quantitative detection of step (b), this takes place in a simple manner by determining the reproduction of the cells at a fixed time or the rate of reproduction of the cells under said conditions. The resulting data are then compared with data obtained on the basis of standard preparations of known concentration, and the concentration of the sample is determined by calculation.

An alternative possibility in this case too is to detect quantitatively the extent of ras signal pathway activation on the basis of the extent of the expression in the cell of a reporter gene which is preferably heterologous to the cell. As explained above, expression thereof is possible only because of the activation, brought about as a result of the activation of the signal pathway connected to a Ras protein, of a specific transcription factor. With this detection variant, the assay preferably takes place under conditions which preclude cell reproduction, for example by using the cdc25-2 yeast mutant at restrictive temperatures, so that the transcribed amount of transcription product of the reporter gene or the expressed amount of reporter protein at a particular time or, alternatively, the expression rate of this reporter gene or protein can be determined with an essentially constant number of cells. However, the quantitative determination may also take place under proliferation conditions if, at the same time, the number of cells is determined continuously or at defined time intervals, and the values found for reporter gene expression are converted into values per unit value of the number of cells.

An alternative possibility in this case too is for quantitative detection to take place via expression of the reporter gene homologous to the host cell, in which case the increase in reporter gene: expression observable at any time compared with the expression level present in cells without activation of the ras signal pathway is used to determine the result or value from each individual test, which is then compared with the values for the other tests to determine the overall result, the ligand concentration.

Another alternative in vivo assay makes it possible to detect whether a compound is able to alter a binding activity of a ligand-binding section of a receptor in relation to a ligand, that is to say to act as agonist, antagonist or inhibitor. This assay is characterized by the following steps:
  (a) contacting the ligand in the presence of the compound with cells of the invention under conditions with which in the absence of the membrane receptor a Ras or Ras-like signal pathway in the cells cannot be activated, where the membrane receptor contains said ligand-binding section, and the effector protein or polypeptide whose binding to a membrane component depends on the binding of a ligand to the ligand-binding section of the membrane receptor defined is able to activate the inactive Ras or Ras-like signal pathway,
  (b) investigating whether and, where appropriate, to what extent activation of the Ras or Ras-like signal pathway takes place,
  (c) comparing the result of the investigation in step
  (b) with a result of an investigation obtained when the assay is carried out in the absence of the compound. In this case, an increased activation of the Ras or Ras-like signal transduction pathway in the presence of the compound indicates an agonist function of this compound, whereas a reduced or, where appropriate, even completely absent activation indicates an antagonist or inhibitory function of the compound.

Step (a) may moreover comprise adding the compound before the ligand to the cells, it being possible where appropriate to preincubate the compound with the cells, adding the compound separately but at the same time as the ligand to the assay cells, or mixing the compound beforehand with the ligand and, where appropriate, carrying out a preincubation of the two compounds, and only then adding the mixture to the assay cells.

If the compound is a peptide, polypeptide or protein, the compound can also be prepared by expressing a gene coding therefor inside the cell itself. For this purpose, the cells can be transformed or transfected with an expression vector which contains such a gene. The means and methods necessary for this are well known to the skilled worker.

If the compound to be tested for its agonistic or antagonistic effect is expressed in the assay cell, then the expression of the gene coding therefor preferably takes place under the control of a constitutively active promoter and with use of cells in which the Ras or Ras-like signal transduction pathway is inactivated only under the specific assay conditions. Such a system makes it possible to preclude expression of the compound in the cell on its own causing changes which might falsify the result of the assay. To preclude this it is necessary to detect under nonrestrictive conditions and in the absence of ligand the activity of the ras signal transduction pathway intrinsic to the cell, which is inactivated under restrictive conditions. Under nonrestrictive conditions and in the absence of ligand the membrane receptor is in an inactive state, so that the detectable activation of the ras signal transduction pathway indicates that the expression product does not interfere with any component of the Ras or Ras-like signal transduction pathway and, in particular, not with the Ras protein or guanine nucleotide exchange factor specific therefor. It is possible in this way to preclude, or minimize the probability, that the expression product interacts with the effector protein or with an adaptor protein which is necessary for binding of the effector protein to the membrane component, instead of with the ligand-binding section of the membrane receptor, so that the ability of the component to activate the Ras or Ras-like signal transduction pathway is abolished.

A corresponding test of activation of the particular Ras or Ras-like signal transduction pathway under nonrestrictive conditions, in the presence of the compound and in the absence of ligand is carried out analogously with a compound added to the assay cells from outside.

If the Ras or Ras-like signal transduction pathway which can be inactivated under the assay conditions is one whose activation is essential for cell reproduction, simply the normal reproducibility of the cells is ensured under nonrestrictive conditions. If detection takes place by use of a reporter gene activity, it is necessary to detect this reporter gene activity under nonrestrictive conditions.

For the detection under the restrictive conditions of the assay in step (b) there is likewise the possibility, for example, of detecting the activation of the signal pathway connected to a Ras protein via the expression, which takes place where appropriate and only on the basis of the activation resulting from the activation of the signal pathway connected to a Ras protein, of a reporter gene heterologous to the cells. The detection of the extent of the activation of the Ras or Ras-like signal pathway which takes place on detection of this activation may comprise a quantitative determination in which the amount, present in the cells, of transcription or translation product (reporter protein) of the reporter gene is determined at a particular time or the reporter gene transcription rate or the reporter protein expression rate is determined under the conditions mentioned.

An alternative possibility is also only to analyze aliquots, i.e. equal volumes of the assay solutions which have been produced and treated identically, apart from the addition of the compound, preferably ensuring equal or essentially equal numbers of cells in these aliquots. In this case the level of reporter gene expression is not quantified absolutely, but only a relative comparison of the levels of expression in the two assays is made possible.

In the case where the comparison in step (c) reveals that stronger expression of the reporter gene occurs in the presence of the compound, the compound is to be assumed to have an agonistic effect, and in the case where the comparison in step (c) reveals that lower expression of the reporter gene occurs in the presence of the compound, the compound is to be assumed to have an antagonistic effect. Like the quantitative assay described above, this assay is also preferably carried out under conditions with which no reproduction of the cells occurs.

An alternative possibility is for the reporter gene employed for the detection also to be homologous to the assay cell, in which case the increase, observable in each instance, in the expression, i.e. transcription and/or translation, of the reporter gene compared with the level of expression present in cells without activation of the Ras or Ras-like signal pathway is used to determine the result.

If the cells employed for the assay are ones in which the inactive signal pathway connected to a Ras protein is a signal pathway which acts on the cell cycle and whose activation is essential for cell reproduction, step (b) comprises to investigate whether and, where appropriate to what extent the cells are capable of reproduction under the conditions mentioned. In the case where the comparison in step (c) reveals that greater cell reproduction occurs in the presence of the compound, the conclusion is that the compound has an agonistic effect, and in the case where the comparison in step (c) reveals that less cell reproduction occurs in the presence of the compound, the conclusion is that the compound has an antagonistic effect.

Like all the assays within the scope of this invention, this assay is also suitable in particular for mass screening, in this case for compounds which are receptor agonists and antagonists.

An alternative possibility is for the assay also to be used as additional test for confirming the ligand-binding property of a novel, in particular synthetic, ligand-binding section or for confirming the suitability of a test substance as ligand for the ligand-binding section. If the ligand-binding section has a ligand-binding property or if the ligand is suitable for the ligand-binding section, it should be observed on use of a known agonist for the ligand employed for the first detection of the ligand property, or for the ligand-binding section that there is increased activation of the Ras or Ras-like signal pathway, and on use of a known antagonist for the ligand or the ligand-binding section that there is in return a reduced activation of the Ras or Ras-like signal pathway.

A further alternative in vivo assay makes it possible to detect whether a polypeptide or protein suspected of a ligand-binding function of a receptor in fact has this function. This assay comprises the following steps:

(a) contacting cells of the invention with the ligand under conditions with which in the absence of the membrane receptor a Ras or Ras-like signal pathway in the cells cannot be activated, where the ligand-binding section of the membrane receptor comprises the polypeptide or protein to be investigated or consists thereof, and where the effector protein or polypeptide whose binding to a membrane component depends on the binding of a ligand to the ligand-binding section of the membrane receptor is able to activate the inactive Ras or Ras-like signal pathway, (b) investigating whether an activation of the Ras or Ras-like signal pathway has taken place.

Detection of the activation of the Ras or Ras-like signal pathway indicates that the ligand-binding section of the membrane receptor and, accordingly, the polypeptide or protein to be investigated has a ligand-binding function of a receptor.

For example, the membrane receptor present in the cells may comprise a ligand-binding section which contains a ligand-binding section derived from a ligand-binding section of a naturally occurring receptor by mutation, or consists thereof.

As previously, it is possible to detect the activation of the Ras or Ras-like signal transduction pathway on use of cells with which the Ras or Ras-like signal transduction pathway which is inactivate at least under certain conditions is a signal pathway which acts on the cell cycle and, whose activation is essential for cell reproduction, on the basis of cell reproduction which takes place where appropriate.

An alternative possibility is to detect the activation of the Ras or Ras-like signal transduction pathway also on the basis of the expression, which can be detected where appropriate, of a reporter gene in the cells. As explained, if the reporter gene is heterologous, expression thereof takes place only on the basis of the activation, resulting from the activation of the Ras or Ras-like signal pathway, of a specific transcription factor. In the case of a homologous reporter gene the aim is to detect the increase in reporter gene expression, e.g. on the basis of larger amounts of transcription or translation product, compared with the expression level without activation of the specific Ras signal transduction pathway.

The assay methods which can be implemented using the second variant, i.e. effector protein or polypeptide translocation onto the cell membrane possible only when there is a lack of ligand binding to the ligand-binding section of the membrane receptor investigated according to the invention, and which are explained in detail hereinafter, can be used, inter alia, for 1. determining the suitability of a test substance as ligand for a receptor and, in this case, in particular carrying out mass screens with ligand derivatives in order to test which derivatives are able to bind to the wild-type ligand-binding section of the receptor,
2. detecting the presence of a particular ligand in a sample,
3. detecting whether a compound is able to change a binding activity of a ligand-binding section of a receptor in relation to a ligand, that is to say to act as agonist, antagonist or inhibitor, and in this case in particular carrying out mass screens for finding such agonistic or antagonistic compounds;
4. detecting the ligand-binding function of a polypeptide or protein suspected of having such a function for ligands of particular receptors; in this case too it is possible for the polypeptides or proteins in particular to be novel ligand-binding sections, derived from natural receptors by mutation, of receptors whose ligand-binding function is yet to be confirmed; in this connection, it is possible in particular to carry out mass screens with such novel mutated ligand-binding sections which [lacuna] for example in the form of a receptor mutant library which contains in particular receptor mutants with randomly localized mutations in the ligand-binding section, in order to find novel artificial, functional ligand-receptor partners.

The aforementioned assays can take place essentially analogously to the assay variants explained previously, using the first variant, but in this case the detection of the activation of the Ras or Ras-like signal pathway indicates the absence of a ligand for the ligand-binding section of the investigated membrane receptor in the assay cell. The latter assays will accordingly usually comprise two detections, specifically one detection in the presence of (potential) ligand, in which case no activation of the Ras or Ras-like signal pathway will be detectable if the (potential) ligand has a ligand-binding property for the ligand-binding section of the membrane receptor investigated according to the invention, and another detection in the absence of the (potential) ligand, in which case such an activation will ordinarily be detected.

In the detection of whether a compound is able to change a binding activity of a ligand-binding section of a receptor in relation to a ligand, that is to say to act as agonist, antagonist or inhibitor, the detection takes place in the simultaneous presence of ligand and compound, in particular via a) the activation, which is possibly in fact detectable if the compound has an antagonistic or inhibitory effect, of the Ras or Ras-like signal pathway, for example with subsequent determination of the ligand concentration necessary for complete inactivity of the Ras or Ras-like signal pathway, at a particular concentration of compound or a determination of the dependence of the signal pathway activation on the concentration of compound at a particular ligand concentration; or
b) the inactivity, which is complete even at a relatively low ligand concentration when the compound has an agonistic effect, of the Ras or Ras-like signal pathway; in this case too it is possible to determine the dependence of the complete inactivity of the Ras or Ras-like signal pathway on the concentration of the compound and/or of the ligand in particular.

In the detection of a ligand-binding function of a polypeptide or protein suspected of such a function for ligands of particular receptors, the detection of the ligand-binding function takes place analogously via the inactivity of the Ras or Ras-like signal pathway in the presence of ligand when this signal pathway is active in the absence of ligand.

Detection of receptor-ligand interactions by means of the assay methods, cells and fusion proteins of the invention is not confined to eukaryotic cells as in vivo test system but can alternatively also take place in prokaryotic cells or in yeasts lacking cell walls, called ghost forms of yeasts.

Depending on the membrane receptor employed and, in particular, depending on the mechanism which depends on the mediator section of the membrane receptor and which eventually leads to a translocation of the effector protein or polypeptide onto the membrane, it may in some embodiments of the invention, as already mentioned hereinbefore, additionally be necessary to provide in the assay cells further conditions which ensure that the detectable translocation event occurs exclusively if there is an interaction of a ligand or, alternatively, if there is a lack of interaction of a ligand with the ligand-binding section of this membrane receptor. Association of the effector protein or polypeptide with membrane-associated cell components which (in the absence of the membrane receptor and of the cell components which cooperate specifically and exclusively with the latter in signal transduction) naturally occur in these cells, irrespective of the state of activation and modification, must be precluded. The precondition for this is that all components directly and indirectly involved in the translocation of the effector protein or polypeptide onto the cell membrane can be rendered capable of mediating or bringing about the binding of the effector protein or polypeptide to a component of the cell membrane only as a result of the activation of the membrane receptor which is to be specifically tested, on the basis of the binding or, alternatively, lack of binding of a ligand to the ligand-binding section and, more accurately, only as a result of the structural change in the mediator section caused by this activation.

If it is intended to test a membrane receptor naturally occurring in a cell in a test, it must be ensured that the mediator section of this membrane receptor occurs in the cell only in conjunction with the latter and that the adaptor and facilitator proteins cooperating therewith can interact only with this mediator section or only because of activation of this mediator section in such a way that translocation of the effector protein or polypeptide onto the cell membrane eventually occurs.

An alternative possibility is for a cell to be selected as assay cell in which, before introduction of the genetic information for the membrane receptor and the adaptor, facilitator and/or effector proteins or polypeptides which are required where appropriate, none of these components naturally occurs, that is to say are heterologous to this initial cell, and no components of the same specificity and, where appropriate, activity which might replace the latter are intrinsically present in the cell either; in relation to the membrane receptor, this may also apply only to the mediator section. Or care must be taken that an initial cell which in an original state once contained these components, in relation to the membrane receptor where appropriate also only the specific mediator section, no longer contains these components because of genetic or other modification before introduction of the genetic information for the membrane receptor and the adaptor, facilitator and/or effector proteins or polypeptides which are required where appropriate. Explained comprehensively, this relates at least to the following components:

the mediator section, where appropriate the adaptor proteins or adaptor protein sections cooperating therewith where binding of the effector protein or polypeptide takes place to the latter or via the latter, and for example in the case of alternative 1)c) explained herein, where appropriate a facilitator component which need not be directly spatially associated with the mediator section of the membrane receptor but is, in the event of ligand binding or, alternatively, lack of ligand binding to the ligand-binding section, activated or modified by the latter and, for this reason, facilitates a secondary event on another component of the cell membrane, as a result of which the effector protein or polypeptide specifically binds to this component of the cell membrane, which is not associated with the mediator section of the membrane receptor; alternatively, said secondary event in the cell may be facilitated only if there is ligand binding or, alternatively, lack of ligand binding of the ligand-binding section of the membrane receptor. Thus, in the latter case, no interaction partners for these facilitators which are able to exert an activation effect corresponding to the membrane receptor on the facilitator(s) must be present in the cell.

If, consequently, a cell system in which the membrane receptor to be tested does not naturally occur is used, it may be necessary to express, besides the membrane receptor, other proteins in this cell system, in particular where appropriate adaptor and/or facilitator proteins or polypeptides.

Concerning the assay conditions, no particular general requirements are necessary. However, in the case of detection of cell reproduction taking place where appropriate, it can thus be taken that the medium used makes this possible in principle. Where it is possible to inactivate genes and/or promoters in the cells, as explained, by choosing particular assay conditions, and inactivation is also intended during the assay, these conditions such as, for example, a particular restrictive assay temperature, in the case of cdc25-2 cells for example 33–37° C., should be maintained during the assay. The chosen reaction medium should moreover not interact with the test compound or the ligand which are added to the medium in any way to impair the assay.

The ligands which can be investigated and determined in all the assay methods explained above are naturally occurring substances such as odorants, flavorings, peptides, peptide hormones and proteins, in particular cytokines, neurotransmitters, non-protein- or -peptide-like hormones, in particular steroid hormones, vitamins, e.g. vitamin D, thyroxine or retinoic acid, as well as substances which do not occur naturally, e.g. synthetic derivatives of natural ligands or toxins/poisons, such as dioxin.

In the majority of cases, the ligand-binding section of the membrane receptor will have an extracellular localization. On use of ligand-binding sections in particular of nuclear receptors, however, there is also the possibility that the latter have an intracellular localization. Since the ligands of nuclear, receptors are mainly small molecules with lower relative molecular mass and mainly hydrophobic nature, they diffuse without further measures into the assay cells of the invention in order to enter into binding therein with a ligand-binding section, which has an intracellular localization directly on the cell membrane, of the membrane receptor. If desired and/or necessary, however, the cells can be pretreated before the assay in a suitable way in order to make the outer cell membrane more permeable for the test compound or the ligand to pass through. One example thereof is the preparation of cell ghosts by, for example, enzymatic treatment of cells. Cell ghosts of this type and those prepared in another way, and cells with a cell wall modified in another way to increase the permeability are also embraced by the term "cells" in the present context.

If the ligands to be tested are peptides, polypeptides or proteins, the latter may also be expressed in the assay cell starting from the nucleic acid constructs which encode the latter and have been introduced into the assay cell, in a special variant also non-constitutively but under the control of an inducible promoter; it is moreover possible for the constructs to be present after introduction into the assay cell chromosomally or extrachromosomally, i.e. as constituent of an episome, e.g. plasmid. The contacting of the assay cell with the ligand accordingly takes place in the case of non-constitutive expression under conditions with which expression of the ligand to be tested is induced in the cell. The skilled worker is aware of a large number of inducible promoters for this purpose, which can be induced, for example, by particular temperatures or chemical compounds. On use of membrane receptors with ligand-binding domains with an extracellular localization, care must additionally be taken that ligands expressed in the assay cell are also secreted from the assay cells into the extracellular space. Various possibilities for this are also known to the skilled worker.

It should in general be stressed that on addition of the ligand to be tested to the assay cell from outside constitutive expression is possible in the assay cell of all the components cooperating in the assay system of the invention, i.e. in particular the membrane receptor to be investigated, as defined in claim 1, the effector protein or polypeptide, any adaptor and where appropriate facilitator proteins or polypeptides, and all the components of the signal pathway which is specifically activated by the effector protein or polypeptide on binding thereof to one component of the membrane and is connected to a Ras protein, which are involved only in this specific signal pathway. On expression of the ligand to be tested in the assay cell it is possible in the first variant, in which an effector protein or polypeptide translocation onto the membrane is detectable only on binding of ligand to the ligand-binding section of the investigated membrane receptor, for all components of the assay system, now including the ligand, apart from one to be constitutively expressed in the assay cell. The assay system component(s) whose gene(s) is or are provided under the control of an inducible promoter is or are then expressed in particular only under assay conditions, i.e. on investigation of the possible activation of the ras signal transduction pathway, on the basis of the specific induction of the inducible promoter or promoters employed in each case. In the second variant, in which the effector protein or polypeptide translocation onto the membrane occurs only when there is a lack of ligand binding to the membrane receptor, on expression of the ligand in the assay cell its gene will always be provided under the control of an inducible promoter in order to make detection possible even in the absence of the ligand.

Detection of the activation of the Ras or Ras-like signal transduction pathway takes place in a manner familiar to the skilled worker depending on the detection strategy. If the cells are immobilized on a solid carrier during the assay, it may be necessary or helpful, in particular in the case of detection of a reporter gene activity or of a reporter protein, to solubilize the cells before the detection reaction, i.e. to detach them from the carrier and, where appropriate, also disintegrate them. The measures and reagents necessary for this purpose are also well known to the skilled worker.

The invention additionally provides kits for use in the assays of the invention, which make it possible, for example, to determine rapidly and efficiently whether a specific ligand is able to bind to a particular receptor and, more accurately, to its ligand-binding section.

A first kit of the invention for use in the assaying methods for determining the suitability of a test substance as ligand for a ligand-binding section of a receptor, for determining the presence of a ligand for a ligand-binding section of a receptor in a sample, for determining the concentration of such a ligand, and for characterizing compounds as possible agonists or antagonists in relation to receptor-ligand interactions comprises in each case cells of the invention with the properties explained above in detail for the assay methods. Thus, the cells in the kit contain, for example when it is intended to detect a reporter gene activity, additionally a construct with a binding site for the transcription factor which is activated specifically through the Ras or Ras-like signal pathway whose activation is to be detected by the assay, with a minimal promoter and with the reporter gene. An alternative possibility is for the kit as well as all following ones to comprise a transformation or transfection vector which contains the construct. It is possible in this way for the user of the kit on choice of this detection route to equip the assay cells present in the kit with this construct by transformation or transfection. In another embodiment of this and all following kits, the transformation or transfection vector provided separately in the kit contains only the binding site for the transcription factor and the minimal promoter functionally linked thereto, and a suitably provided insertion site for the insertion of a reporter gene which can be chosen freely by the user.

In addition, this kit, as well as all following ones, may contain inter alia where appropriate also assay buffers, reagents for detecting the phenotypical activation of the Ras or Ras-like signal transduction pathway in these cells and/or instructions for use.

An alternative kit for the aforementioned assay methods comprises at least two of the following components:
(a) cells in which at least under certain conditions a Ras or Ras-like signal pathway cannot be activated;
(b) a nucleic acid vector into which is expressibly inserted a DNA sequence which encodes a membrane receptor, as defined above, where the effector protein or polypeptide whose binding to a membrane component depends on the binding or, alternatively, lack of binding of a ligand to the ligand-binding section of the membrane receptor is able to activate the inactive Ras or Ras-like signal pathway in the cells mentioned under (a);
(c) a nucleic acid vector into which is expressibly inserted a DNA sequence which encodes the effector protein or polypeptide which, in the event of ligand binding or, alternatively, lack of ligand binding to the ligand-binding section of the membrane receptor, is able to bind to a component of the membrane, where appropriate via other proteins or polypeptides;
(d) a nucleic acid vector into which is expressibly inserted a DNA sequence which encodes at least one adaptor protein, via which the effector protein or polypeptide is able, when there is binding, or, alternatively, lack of binding of a ligand to the ligand-binding section of the membrane receptor, to bind to a component of the membrane.

Another alternative kit for the aforementioned assays makes it possible with a particular choice of the components listed hereinafter in particular to prepare the assay cell with a membrane receptor which contains an individually desired ligand-binding section. The kit comprises at least two of the following components:
(a) cells in which a Ras or Ras-like signal pathway cannot be activated at least under certain conditions;
(b) a nucleic acid vector which comprises, in suitable arrangement:
    a DNA section which encodes a membrane-localization signal of a membrane receptor as defined above in connection with the membrane receptor;
    a DNA section which encodes a mediator section of a membrane receptor as defined above in connection with the membrane receptor; and
    a suitably arranged insertion site for functional insertion of a DNA sequence which encodes a ligand-binding section of a receptor, where, after insertion of a DNA sequence for the ligand-binding section, the nucleic acid vector comprises a complete expressible gene for a membrane receptor as defined above, where the effector protein or polypeptide whose binding to a membrane component depends on the binding or, alternatively, lack of binding of a ligand to the ligand-binding section of the membrane receptor is able to activate the inactive Ras or Ras-like signal pathway in the cells mentioned under (a);
(c) a nucleic acid vector into which is expressibly inserted a DNA sequence which encodes the effector protein or polypeptide which, in the event of ligand binding or, alternatively, lack of ligand binding to the ligand-binding section of the membrane receptor, is able to bind to a component of the membrane, where appropriate via other proteins or polypeptides;
(d) a nucleic acid vector into which is expressibly inserted a DNA sequence which encodes at least one adaptor protein, via which the effector protein or polypeptide is able, when there is binding, or, alternatively, lack of binding of a ligand to the ligand-binding section of the membrane receptor, to bind to a component of the membrane.

In a specific embodiment it applies to the two latter kits that component (c) of the kit comprises a nucleic acid vector whose DNA sequence encodes an effector protein or polypeptide in the form of a fusion protein composed of an effector section and of an adaptor protein or polypeptide which makes binding possible to a component of the membrane, where appropriate via other proteins or polypeptides.

In another specific embodiment of component (c) of the two latter kits, the nucleic acid vector present therein comprises a DNA sequence which encodes an effector protein or polypeptide in the form of a fusion protein composed of an effector section and of an antibody or binding protein section with specific binding affinity for a tag or epitope structure which is present on the membrane receptor and becomes accessible for the antibody or the binding protein only because of conformational changes, where appropriate in combination with enzymatic activity, resulting from binding of ligand or, alternatively, lack of binding of ligand to the ligand-binding section of the membrane receptor.

It also applies additionally to the two latter assays that the cells present in the kit may, for an intended detection of a reporter gene activity inter alia additionally also contain a construct comprising a binding site for a transcription factor whose activation results from the activation of the specific Ras or Ras-like signal pathway whose activation is to be detected by the assay, a minimal promoter and the reporter gene as explained above, or it is possible alternatively to provide, separately from the cells, a transformation or transfection vector with the transcription factor binding site-minimal promoter-reporter gene construct or with another type of construct comprising the transcription factor binding site and the minimal promoter and, in addition, a suitably arranged insertion site for a reporter gene which can be chosen freely.

The invention also provides kits for the assay methods of the invention for detecting whether a polypeptide or protein has a ligand-binding function of a receptor.

A kit suitable for this purpose comprises cells of the invention, and the membrane receptor present therein comprises a ligand-binding section comprising or consisting of a polypeptide or protein suspected of having a ligand-binding function of a receptor.

An alternative kit comprises at least two of the following components:
(a) cells in which a Ras or Ras-like signal pathway cannot be activated at least under certain conditions;
(b) a nucleic acid vector into which is expressibly inserted a DNA sequence which encodes a membrane receptor as defined above, where the ligand-binding section of the membrane receptor comprises a polypeptide or protein suspected of having a ligand-binding function of a receptor, or is formed therefrom, and the effector protein or polypeptide whose binding to a membrane component depends on the binding or, alternatively, lack of binding of a ligand to the ligand-binding section of the membrane receptor is able to activate the inactive Ras or Ras-like signal pathway in the cells mentioned under (a);
(c) a nucleic acid vector into which is expressibly inserted a DNA sequence which encodes the effector protein or polypeptide which, in the event of ligand binding or, alternatively, lack of ligand binding to the ligand-binding section of the membrane receptor, is able to bind to a component of the membrane, where appropriate via other proteins or polypeptides;
(d) a nucleic acid vector into which is expressibly inserted a DNA sequence which encodes at least one adaptor protein, via which the effector protein or polypeptide is able, when there is binding, or, alternatively, lack of binding of a ligand to the ligand-binding section of the membrane receptor, to bind to a component of the membrane.

An alternative kit for use in said assay makes it possible, on specific selection of the components indicated hereinafter, inter alia for an assay cell to be equipped specifically with a membrane receptor which comprises as ligand-binding section a polypeptide or protein which is desired by the user of the kit and is to be investigated for its ligand-binding function. Such a kit comprises at least two of the following components:
(a) cells in which a Ras or Ras-like signal pathway cannot be activated at least under certain conditions;
(b) a nucleic acid vector which comprises, in suitable arrangement:
  a DNA section which encodes a membrane-localization signal of a membrane receptor as defined above in connection with the membrane receptor;
  a DNA section which encodes a mediator section of a membrane receptor as defined above in connection with the membrane receptor; and
  a suitably arranged insertion site for functional insertion of a DNA sequence which encodes a polypeptide or protein suspected of having a ligand-binding function of a receptor, where, after insertion of a DNA sequence for the ligand-binding section, the nucleic acid vector comprises a complete expressible gene for a membrane receptor, where the effector protein or polypeptide whose binding to a membrane component depends on the binding or, alternatively, lack of binding of a ligand to the ligand-binding section, formed from the polypeptide or protein suspected of having a ligand-binding function or a receptor of the membrane receptor is able to activate the inactive Ras or Ras-like signal pathway in the cells mentioned under (a);
(c) a nucleic acid vector into which is expressibly inserted a DNA sequence which encodes the effector protein or polypeptide which, in the event of ligand binding or, alternatively, lack of ligand binding to the ligand-binding section of the membrane receptor, is able to bind to a component of the membrane, where appropriate via other proteins or polypeptides;
(d) a nucleic acid vector into which is expressibly inserted a DNA sequence which encodes at least one adaptor protein, via which the effector protein or polypeptide is able, when there is binding, or, alternatively, lack of binding of a ligand to the ligand-binding section of the membrane receptor, to bind to a component of the membrane.

It also applies to the two latter kits that, in a specific embodiment, component (c) of the kit comprises a nucleic acid vector whose DNA sequence encodes an effector protein or polypeptide in the form of a fusion protein composed of an effector section and an adaptor protein or polypeptide which makes binding possible to one component of the membrane, where appropriate via other proteins or polypeptides.

Likewise, in another specific embodiment of component (c) of the two latter kits, the nucleic acid vector contained therein comprises a DNA sequence which encodes an effector protein or polypeptide in the form of a fusion protein composed of an effector section and an antibody or binding protein section with specific binding affinity for a tag or epitope structure which is present on the membrane receptor and which becomes accessible for the antibody or the binding protein only because of conformational changes, where appropriate in combination with enzymatic activity, resulting from binding of ligand to the ligand-binding section of the membrane receptor or, alternatively, dissociation of the ligand of the ligand-binding section, i.e. lack of binding of ligand to the ligand-binding section of the membrane receptor.

If it is intended to detect a reporter gene activity, in one embodiment the cells in the aforementioned kits additionally contain a construct comprising a binding site for a transcription factor whose activation results from activation of the specific ras signal pathway whose activation is to be detected by the assay, a minimal promoter and the reporter gene, as explained above, or it is possible alternatively to provide, separately from the cells, a transformation or transfection vector with the transcription factor binding site-minimal promoter-reporter gene construct or with another type of construct comprising the transcription factor binding site and the minimal promoter and, in addition, a suitably arranged insertion site for a reporter gene which can be chosen freely.

It is additionally possible for all the kits of this invention in possible embodiments to comprise inter alia additionally at least one of the following components:

(b) where appropriate a nucleic acid vector into which is expressibly inserted a DNA sequence which encodes at least one facilitator protein which need not be directly spatially associated with the mediator section of the membrane receptor but is, in the event of ligand binding or, alternatively, lack of ligand binding to the ligand-binding section of the membrane receptor, activated or modified by this mediator section and, for this reason, facilitates a secondary event on another component of the cell membrane, as a result of which the effector protein or polypeptide specifically binds to this component of the cell membrane, which is not associated with the mediator section of the membrane receptor;

(f) where appropriate reagents for the transformation or transfection of the cells with transformation or transfection vector(s), (g) where appropriate reagents for detection of the phenotypical activation of the signal transduction pathway connected to a Ras protein in these cells.

In a preferred embodiment of the invention, the kits of the invention comprise the cells immobilized on a solid carrier, as explained above, in particular on biochips (cf. Wolf et al. 1997 and 1998). Immobilization of the cells on biochips, and in the individual wells of microtiter plates, is particularly suitable for mass screens and, in particular, high-throughput methods for detecting and measuring membrane receptor-ligand interactions, so that a plurality of separate assay methods can be carried out on such a plate. It is also possible in this connection to provide different cells of the invention, i.e. in particular cells with different ligand-binding section, in wells in respectively defined sections on one and the same microtiter plate.

If the cells in the kit are immobilized on a solid carrier it may be necessary or helpful, in particular on detection of a reporter gene activity or transcription of a reporter protein, to solubilize the cells before the detection reaction, i.e. detach them from the carrier and, where appropriate, also disintegrate them. In this case it is possible for the reagents mentioned under g) for detecting the phenotypical activation of the Ras or Ras-like signal transduction pathway also to comprise suitable solubilizing reagents which, in particular, contain one or more surface-active agents or surfactants.

The invention also extends to
ligands for a binding section of a receptor,
compounds which are able to alter a binding activity of a ligand-binding section of a receptor in relation to a ligand (referred to as "modifying compounds" hereinafter) and
polypeptides or proteins having a ligand-binding function of a receptor, which have been determined or found by means of one of the assay methods of the invention, and compositions containing these ligands, compounds and/or polypeptides or proteins.

In relation to polypeptides or proteins having a ligand-binding function of a receptor and having been derived from a naturally found or synthetically produced molecule for production of the membrane receptor as defined in claim 1, the invention comprises both the fragment which is present in the membrane receptors employed according to the invention and has a ligand-binding function, and the initial fragment or molecule. It may be remarked in relation to this, only for the sake of clarity, that the production of the membrane receptor usually takes place by expression of a nucleic acid sequence encoding this membrane receptor in a cell. A polypeptide or protein with ligand-binding function of a receptor is accordingly derived from a larger initial molecule usually in an analogous way at the nucleic acid level, by merely using one or more sections of the nucleic acid sequence encoding the initial molecule, where appropriate with subsequent cloning for attachment of sections which encode other membrane receptor components or sections, for expression of the membrane receptor. The deriving may also include one or more slight nucleic acid sequence modifications in the initial sequence or in the nucleic acid section(s), preferably of a type such that the resulting nucleic acid molecule still hybridizes under stringent conditions with the respective initial nucleic acid molecule.

The invention accordingly also comprises a method for identifying polypeptides or proteins, in particular receptors, which have a ligand-binding function of a receptor, which comprises:

preparing a cell of the invention with a membrane receptor having the features described in claim 1 and comprising the whole of such a polypeptide or protein or a part of such a polypeptide or protein which presumably contains the sequence sections essential for the ligand-binding function, and using this cell to carry out the in vivo assay, method of the invention for detecting whether a polypeptide or protein has a ligand-binding function of a receptor.

and the molecules identified by this method.

The invention likewise extends to
the use of the aforementioned ligands, modifying compounds and polypeptides or proteins, identified by the assay methods of the invention, as pharmaceuticals, where appropriate after formulation with excipients and/or carriers customary in this sector, and
the use of the ligands, modifying compounds and polypeptides or proteins as lead substances for developing ligands, modifying compounds and polypeptides or proteins which are derived therefrom—in particular by derivatization—in particular those with corresponding or improved activity compared with the respective lead substance.

Thus, the invention also comprises a method for preparing ligands, modifying compounds, polypeptides or proteins by derivatization one or more times starting from ligands, modifying compounds, polypeptides or proteins identified by the assay methods of the invention. This method may comprise, where appropriate, additionally the steps of also testing the ligands, modifying compounds, polypeptides or proteins obtained by the derivatization, using the assay methods of the invention, for ligand function or ligand-binding function and/or formulating the ligands, modifying compounds, polypeptides or proteins obtained by the derivatization, as pharmaceutical in conventional way.

The invention further extends also to the ligands, modifying compounds, polypeptides and proteins obtained by this method, i.e. the functional derivatives obtained by this method.

For a use as gene therapeutic agents intended to bring about the expression of a polypeptide or protein which has a ligand-binding function of a receptor, preferably of a receptor, in particular in human or animal cells, the invention further comprises nucleic acid molecules which are obtained, starting from a polypeptide or protein, in particular receptor, identified by the assay, identification, screening or preparation methods of the invention, by a method which comprises the provision of the gene encoding the polypeptide or protein, or a part, which comprises at least the nucleic acid sequence sections essential for the activity of the encoded polypeptide or protein, of this gene, in essentially pure form, i.e. in particular essentially free of other nucleic acids which are unnecessary or even deleterious for use as gene therapeutic agent. This method may, if not yet known, require preceding identification of the gene which encodes this polypeptide or protein. In particular, the method may additionally also comprise the following steps:

if not yet known, determination of the amino acid sequence of the polypeptide or protein, in particular receptor, and/or if not yet known, identification of the gene which encodes this polypeptide or protein, and determination at least of the sequence of the coding sections of this gene, where appropriate carrying out modifications in the resulting nucleic acid sequence, for example for adaptation of the codon usage to that of a desired recipient organism, for introducing mutations or deleting intron sequences, and formulation of the nucleic acid sequence which has been modified where appropriate in the form of a gene therapeutic agent.

In a currently preferably used experimental system of the invention, the yeast strain cdc25-2 is used as cell system which is inactive in a ras or ras-like signal transduction pathway. As explained, the Ras protein is non-functional (Broder et al., 1998) in these cells at a restrictive temperature of 33–37° C., typically 36° C., as a consequence of the absence of a functional guanine nucleotide exchange factor (GEF; "guanyl nucleotide exchange factor"). Activation of the ras signal transduction pathway which is non-functional in this system at restrictive temperatures can be caused under these conditions only via the translocation, which can be brought about by various measures as described, of an effector protein or polypeptide able to activate this ras signal transduction pathway onto the cell membrane and can be detected by the fact that the yeast cells are able to grow irrespective of the presence of a functional GEF protein at restrictive temperatures (33–37° C., typically 36° C.). As explained, the translocation of the effector protein or polypeptide requires the presence of a suitable ligand for the membrane receptor specifically provided in the cell.

In this system there is use in particular of a fusion protein which comprises as effector section a mutated human Ras protein (Ha-Ras, L61) lacking the farnesylation sequence which ensures membrane localization of the protein.

The examples which are indicated hereinafter by way of example are intended to illustrate the invention further.

Figure 3:
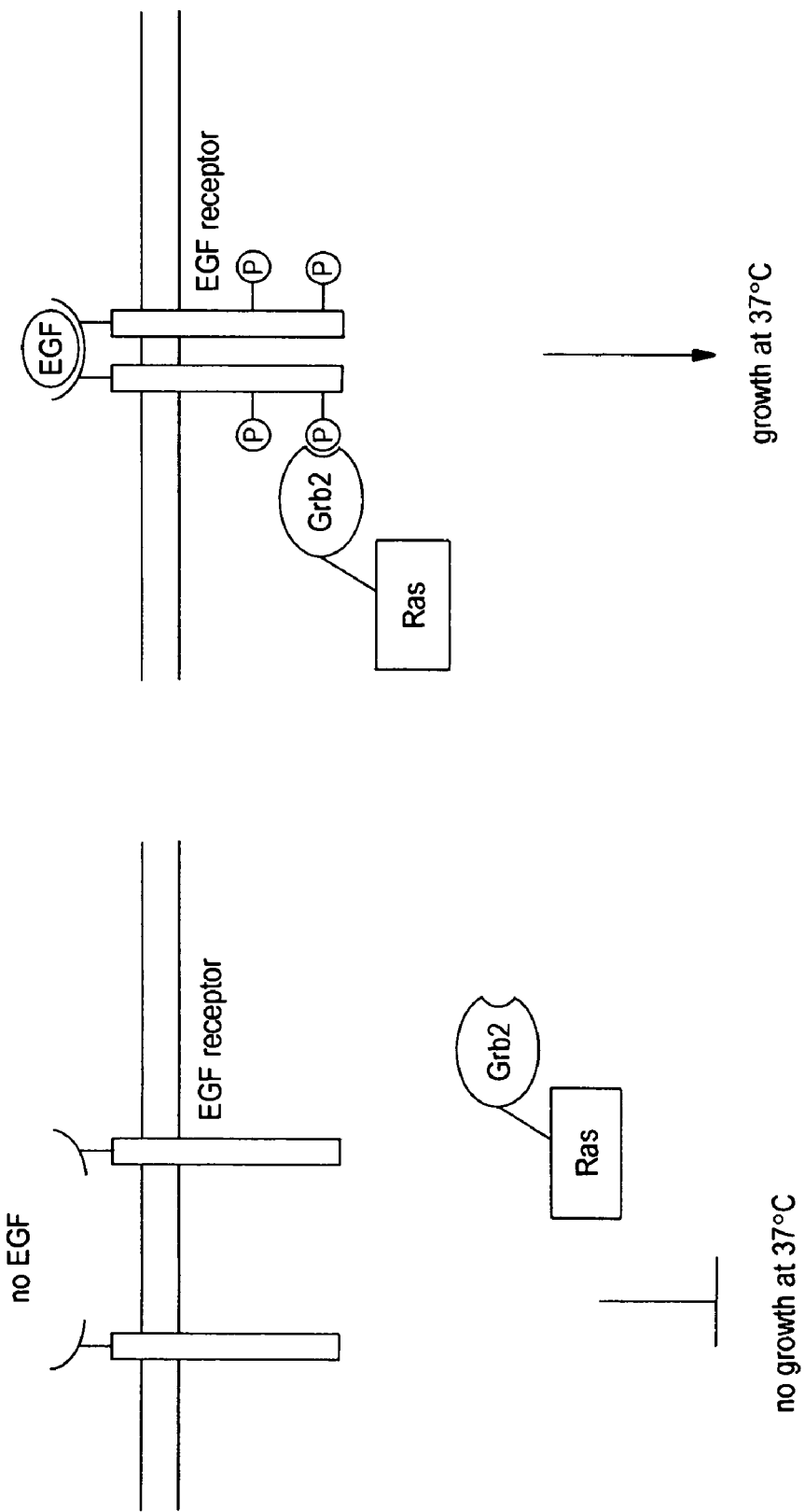
FIG. 3. Diagrammatic representation of the detection of the interaction of EGF with the EGF receptor.

1. Epidermal Growth Factor (EGF) Interaction with the EGF Receptor (FIG. 3)

Material and Methods

The following two vectors are used to transform *Saccharomyces cerevisiae* cdc25-2 cells:

1. An expression vector for constitutive expression of the human EGF receptor protein.

2. An inducible expression vector with a galactose-inducible promoter (Gal 1) for expressing the adaptor-effector fusion protein consisting of the human constitutively active ras protein part (Ha-ras, L61) lacking the so-called. CAAX box (the farnesylation signal for membrane localization) (=effector section) and of the murine Grb2 protein part (=adaptor section).

Yeast Growth and Manipulation

Conventional yeast transformation and manipulation protocols (see, for example, Hill et al. (1991), NAR 19, 5791) were used. The cells were plated out either on a glucose minimal medium which contains the necessary amino acids and nucleotides (20 mg/l histidine, 100 mg/l leucine, 20 mg/l tryptophan, 20 mg/l uracil, 10 mg/l adenine sulfate), 2% glucose, 0.5% $NH_4SO_4$, 0.17% yeast extract and 4% agar, or on galactose medium (1.7 g/l yeast nitrogen without amino acids, 5 g/l ammonium sulfate, 30 g/l galactose (>99%) 20 g/l D-raffinose, 20 g/l glycerol (100%), 30 g/l Bacto Agar).

Replica platings are carried out with velvet replica plater. After transformation with the two expression vectors described above, the cells are plated out on glucose plates and incubated at 25° C. (non-restrictive temperature) for 3–4 days. Various test media (with and without EGF, or with synthetic protein fragments with ligand activity—see Komoriya et al., 1984) are then inoculated with in each case three independent clones and incubated at 37° C. for 2–3 days, and then the growth of the yeasts in the various liquid media is detected. Yeasts which grow in galactose medium at 37° C. only in the presence of EGF (culture of yeast ghost cells lacking cell walls) or only in the presence of [S-acetamidomethyl $Cys^{20,31}$]-EGF-(20-31), an active EGF fragment, indicate functional ligand-receptor interaction.

Figure 4:
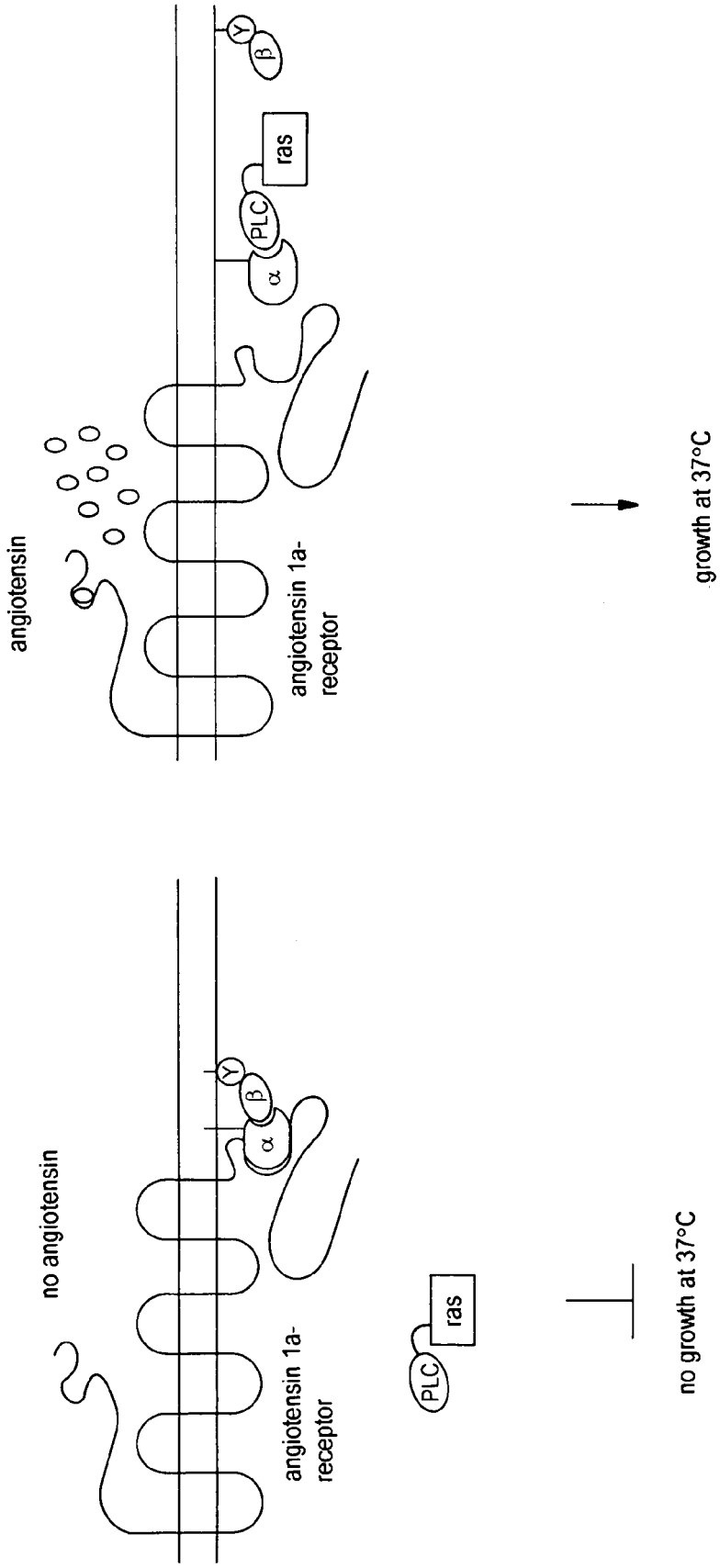
FIG. 4. Diagrammatic representation of the detection of the interaction between angiotensin and the angiotensin 1a receptor.

2. Angiotensin Interaction with the Angiotensin Receptor (FIG. 4)

Material and Methods

The following vectors are used to transform *Saccharomyces cerevisiae* cdc 25-2 cells:

1. An expression vector for constitutive expression of the rat AT1A angiotensin receptor (Condon et al., 1997)

2. One or more expression vectors for constitutive expression of the three rat G-proteins $G\alpha_{13}$, $G\beta_1$ and $G\gamma_3$ (Macrez-Leprêtre et al., 1997).

3. An inducible expression vector (Ura selection marker) with a galactose-inducible promoter (Gal1) for expression of the adaptor-effector fusion protein consisting of phosphatidylcholine phospholipase C minus the domain with the membrane-localization signal (=adaptor section) from rat vascular myocytes (Macrez-Leprêtre et al., 1996) and the human constitutively active ras protein portion (Ha-ras L61) lacking the so-called CAAX box (the farnesylation signal for membrane localization) (=effector section).

Yeast Growth and Manipulation

This corresponds to Example 1. The test media used for the angiotensin receptor experiments were employed plus/minus angiotensin or plus/minus L-162,313, a functional non-protein ligand of the angiotensin receptor (Perlmann et al., 1995). Yeasts which grow after 2 to 3 days at 37° C. in galactose medium only in the presence of angiotensin (culture of yeast ghost cells lacking cell walls) or only in the presence of the non-protein ligand L-162,313 indicate functional ligand-receptor interaction.

REFERENCES

Broder, Y. C., Katz, S. and Aronheim, A. (1998). Curr. Biol. 8, 1121–1124
Conchon, S., Barrault, M.-B., Miserey, S., Corvol, P. and Clauser, E. (1997). J. Biol. Chem. 272, 25566–25572
Current Protocols in Molecular Biology, 1991
Dohlman, H. G., Thorner, J., Caron, M. G. Leifkowitz, R. J. (1991). Ann. Rev. Biochem. 60, 653–688
Komoriya, A., Hortsch, M., Meyers, C., Smith, M., Kanety, H. and Schlessinger, J. (1984) Proc. Natl. Acad. Sci. USA 81, 1351–1355
Leurs, R., Smit, M. J., Alewijnse, A. E. and Timmermann, H. (1998). TIBS 23, 418–422
Macrez-Leprêtre, N., Morel, J.-L. and Mironneau, J. (1996) J. Pharmacol. Exp. Ther. 278, 468–475
Macrez-Leprêtre, N., Kalkbrenner, F., Morel, J.-L., Schultz, G. and Mironneau, J. (1997). J. Biol. Chem. 272, 10095–10102
Nishida, E. and Gotoh, Y. (1993). Trends Biochem. Sci 18, 128–130
Perlmann, S., Shambye, H. T., Rivero, R. A., Greenlee, W. J., Hjorth, S. A. and Schwartz, T. W. (1995). J. Biol. Chem. 270, 1493–1496
Sambrook, J., Fritsch, E. F., Maniatis, T. (1989), Molecular Cloning. A Laboratory Handbook, Cold Spring Harbor Laboratory, New York
Schlessinger, J. and Ulrich, A. (1992). Neuron 9, 383–391
Schlessinger, J. (1993). Trends Biochem. Sciences 18, 273–275
Stahl, N. and Yancopoulos, G. D. (1993) Cell 74, 587–590
Wolf, B., Kraus, M., Baumann, W., Brischwein, M., Ehret, R., Henning, T., Lehmann, M. and Schwinde, A., (1997). BioTec 6/97, 26–29
ibid (1998). BioTec 1/98, 24–27

What is claimed is:

1. An isolated transformed yeast cell comprising, a human epidermal growth factor (EGF) membrane receptor and a fusion protein comprising an effector polypeptide which is a constitutively active human ras polypeptide fused to an adaptor polypeptide which is Grb2 polypeptide, wherein upon binding of ligand to said receptor, said fusion protein binds to said receptor via said adaptor polypeptide, and wherein said fusion protein is capable of activating a Ras-signaling pathway in said cell upon binding of ligand to said EGF receptor.

2. A cell as claimed in claim 1, wherein the receptor is a tyrosine kinase.

3. A cell as claimed in claim 1, wherein said cell is immobilized on a solid carrier.

4. A cell as claimed in claim 3, wherein the cell is immobilized on biochips or enclosed in microchambers.

5. A cell as claimed in claim 1, wherein in the absence of the membrane receptor a Ras signal pathway in the cell cannot be activated.

6. A cell as claimed in claim 5, wherein the activatability of the Ras signal pathway is temperature-dependent in the absence of the membrane receptor.

7. A cell as claimed in claim 6, wherein the lack of activatability of the Ras signal pathway in the absence of the membrane receptor above a particular temperature is derived from at least one mutation of a guanine nucleotide exchange factor intrinsic to the cell, which has the effect that the latter is incapable of functioning above the particular temperature.

8. A cell as claimed in claim 7, wherein the cells are cells of the Saccharomyces cerevisiae yeast strain cdc25-2 or are derived therefrom.

9. A cell as claimed in claim 6, wherein the lack of activatability of the Ras signal pathway in the absence of the membrane receptor above a particular temperature is derived from at least one mutation of a Ras protein intrinsic to the cell, which has the effect that the latter is incapable of functioning above the particular temperature.

10. An in vivo assay for determining the suitability of a test substance as ligand for a ligand-binding section of a receptor, characterized by the following steps:
(a) contacting the test substance with cells as claimed in claim 5 under conditions with which a Ras signal pathway in the cell cannot be activated in the absence of the membrane receptor, where the membrane receptor contains a ligand-binding section, and the fusion protein whose binding to the membrane receptor depends on the binding of a ligand to the ligand-binding section of the membrane receptor is able to activate this Ras signal pathway,
(b) investigating whether activation of the Ras signal pathway has taken place, where detection of the activation of the Ras signal pathway indicates the ability of the test substance to bind to the ligand-binding section.

11. An assay as claimed in claim 10, where step (b) comprises detecting the activation of the Ras signal pathway via reporter gene expression which takes place where appropriate and only because of the activation, resulting from the activation of the Ras signal pathway, of a specific transcription factor, where detection of the expression of the reporter gene indicates the ability of the test substance to bind to the ligand-binding section.

12. An assay as claimed in claim 10, wherein the test substance is a naturally occurring substance, an odorant, flavoring, peptide, peptide hormone, protein, cytokine, growth factor, neurotransmitter, non-protein- or -peptide-like hormone and/or a vitamin.

13. An assay as claimed in claim 10, wherein the test substance is a non-naturally occurring substance a synthetic derivative of a natural ligand, a poison or dioxin.

14. An assay as claimed in claim 13, wherein the test substance is a fusion protein comprising a ligand domain capable of binding to said membrane receptor.

15. A screening method for testing the suitability of a plurality of test substances as ligands for a ligand-binding domain of a receptor, characterized in that the assay method of claim 10 is employed for the screening.

16. An in vivo assay for determining the presence of a ligand for a ligand-binding section of a receptor in a sample which possibly contains the latter, characterized by the following steps:
(a) contacting the sample with cells as claimed in claim 5 under conditions with which a Ras signal pathway in the cell cannot be activated in the absence of the membrane receptor, where the membrane receptor contains a ligand-binding section, and the fusion protein whose binding to the membrane receptor depends on the binding of a ligand to the ligand-binding section of the membrane receptor, is able to activate this Ras signal pathway,
(b) investigating whether activation of the Ras signal pathway has taken place, where detection of the activation of the Ras signal pathway indicates the presence of a ligand for the ligand-binding section of a receptor in the sample.

17. An assay as claimed in claim 16, where step (b) comprises detecting the activation of the Ras signal pathway via reporter gene expression which takes place where appropriate and only because of the activation, resulting from the activation of the Ras signal pathway, of a specific transcription factor, where detection of the expression of the reporter gene indicates the presence of a ligand for the ligand-binding section of a receptor in the sample.

18. A screening method for unknown ligands of a particular receptor in a sample, characterized in that an assay method as claimed in claim 16 is employed for the screening.

19. A kit for use in an assay as claimed in claim 10, which further comprises isolated transformed yeast cells comprising, a human epidermal growth factor (EGF) membrane receptor and a fusion protein comprising an effector polypeptide which is a constitutively active human ras polypeptide fused to an adaptor polypeptide which is Grb2 polypeptide, wherein upon binding of ligand to said receptor, said fusion protein binds to said receptor via said adaptor polypeptide, and wherein said fusion protein is capable of activating a Ras-signaling pathway in said cell upon binding of ligand to said EGF receptor.

20. A cell as claimed in claim 1, wherein the cell is a yeast cell lacking cell walls.

21. A cell as claimed in claim 1, wherein the cell is a *Saccharomyces cerevisiae* yeast cell.

22. A cell as claimed in claim 1, wherein the cell is a *Saccharomyces cerevisiae* yeast cell strain cdc25-2.

23. A cell as claimed in claim 1, wherein the membrane receptor is coded for by a nucleic acid which has been introduced into said cell.

24. A cell as claimed in claim 1, where the fusion protein is coded for by a nucleic acid which has been introduced into said cell.

25. A cell as claimed in claim 1, wherein the fusion protein comprises a constitutively active human ras polypeptide fused to a murine Grb2 polypeptide.

26. A cell as claimed in claim 25, wherein the ras protein lacks the CAAX box.

* * * * *

UNITED STATES PATENT AND TRADEMARK OFFICE
CERTIFICATE OF CORRECTION

PATENT NO.         : 7,029,905 B1                                  Page 1 of 1
APPLICATION NO.    : 09/869709
DATED              : April 18, 2006
INVENTOR(S)        : Albrecht E. Sippel It is certified that error appears in the above-identified patent and that said Letters Patent is hereby corrected as shown below:

On Title page, item [76] Inventors reads "Albright E. Sippel" should read -- Albrecht E. Sippel --
On Title page, item [22] PCT Filed reads "Dec 20, 1999" should read -- Dec 29, 1999 --
On Title page, item [86] PCT No. reads "10400" should read --10460 --
Column 42, line 48-50 reads "A screening method for testing the suitability of a plurality of test substances as ligands for a ligand-binding domain of a receptor, characterized in that the assay method of claim 10 is employed for the screening" should read -- A screening method for unknown ligands of a particular receptor, characterized in that an assay method as claimed in claim 10 is employed for the screening --

Signed and Sealed this

Twenty-third Day of January, 2007

JON W. DUDAS
*Director of the United States Patent and Trademark Office*